(12) United States Patent
Shen et al.

(10) Patent No.: US 10,820,580 B2
(45) Date of Patent: Nov. 3, 2020

(54) IMMUNODEFICIENT NON-HUMAN ANIMAL

(71) Applicant: Beijing Biocytogen Co., Ltd., Beijing (CN)

(72) Inventors: Yuelei Shen, Beijing (CN); Yang Bai, Beijing (CN); Meiling Zhang, Beijing (CN); Jiawei Yao, Beijing (CN); Rui Huang, Beijing (CN); Yanan Guo, Beijing (CN)

(73) Assignee: Beijing Biocytogen Co., Ltd, Beijing (CN)

( * ) Notice: Subject to any disclaimer, the term of this patent is extended or adjusted under 35 U.S.C. 154(b) by 0 days.

(21) Appl. No.: 16/435,080

(22) Filed: Jun. 7, 2019

(65) Prior Publication Data
US 2019/0320631 A1  Oct. 24, 2019

Related U.S. Application Data

(63) Continuation of application No. PCT/CN2018/079365, filed on Mar. 16, 2018.

(30) Foreign Application Priority Data

Mar. 17, 2017 (CN) .......................... 2017 1 0160547
Mar. 15, 2018 (CN) .......................... 2018 1 0215804

(51) Int. Cl.
*A01K 67/027* (2006.01)
*C07K 14/715* (2006.01)
*A61K 49/00* (2006.01)

(52) U.S. Cl.
CPC ...... *A01K 67/0276* (2013.01); *A01K 67/0275* (2013.01); *C07K 14/7155* (2013.01); *A01K 67/0271* (2013.01); *A01K 2207/12* (2013.01); *A01K 2217/075* (2013.01); *A01K 2217/15* (2013.01); *A01K 2227/105* (2013.01); *A01K 2267/0331* (2013.01); *A61K 49/0008* (2013.01); *C12N 2310/20* (2017.05)

(58) Field of Classification Search
CPC ............ A01K 67/0276; A01K 67/0275; A01K 67/0271; A01K 2207/12; A01K 2217/075; A01K 2217/15; A01K 2227/105; A01K 2267/0331; C07K 14/7155; C12N 2310/20; A61K 49/0008
USPC ..................................... 800/18, 13, 21, 24, 3
See application file for complete search history.

(56) References Cited

U.S. PATENT DOCUMENTS

| 4,683,195 A | 7/1987 | Mullis et al. |
| 7,145,055 B2 | 12/2006 | Ito et al. |
| 2015/0106961 A1 | 4/2015 | Rojas et al. |

FOREIGN PATENT DOCUMENTS

| CN | 101809156 | 8/2010 |
| CN | 103409468 | 11/2013 |
| CN | 104561095 | 4/2015 |
| CN | 106119284 | 11/2016 |
| CN | 106755115 | 5/2017 |
| WO | WO 2015155904 | 10/2015 |
| WO | WO 2016168212 | 10/2016 |
| WO | WO2018001241 | 1/2018 |
| WO | WO2018041118 | 3/2018 |
| WO | WO2018041119 | 3/2018 |
| WO | WO2018041120 | 3/2018 |
| WO | WO2018041121 | 3/2018 |
| WO | WO2018068756 | 4/2018 |

OTHER PUBLICATIONS

DiSanto et al. (1995) P.N.A.S., vol. 92, 377-381.*
Schultz et al. (2014) Cold Spring Harb. Protoc., vol. 7, 694-708 (pp. 1-24).*
Cheah et al. (2001) vol. 19, 297-304.*
Noguchi et al. (1993) J. Biol. Chem., vol. 268(18), 13601-13608.*
DiSanto et al. (1994) Eur. J. Immunol., vol. 24, 3014-3018.*
Hsu et al. (2013) Nat. Biotech., vol. 31(9), 827-832.*
Henthorn et al., "IL-2Rγ gene microdeletion demonstrates that canine X-linked severe combined immunodeficiency is a homologue of the human disease," Genomics, 1994, 23(1):69-74.
International Search Report and Written Opinion in International Appln. No. PCT/CN2018/079365, dated Jun. 11, 2018, 11 pages.
Ishikawa et al., "Development of functional human blood and immune systems in NOD/SCID/IL2 receptor γ chainnull mice," Blood, 2005, 106(5):1565-1573.
Katano et al., "NOD-Rag2null IL-2Rγnull mice: an alternative to NOG mice for generation of humanized mice," Experimental animals, 2014, 63(3):321-330.
Liao et al., "IL1-2 family cytokines: new insights into the complex roles of IL-2 as a broad regulator of T helper cell differentiation," Current opinion of immunology, 2011, 23(5):598-604.
Mou et al., "A novel deletion mutation in IL2RG gene results in X-linked severe combined immunodeficiency with an atypical phenotype," Immunogenetics, 2016, 69:29-38.
Noguchi et al., "Interleukin-2 receptor gamma chain. A functional component of the interleukin-7 receptor," Science, 1993, 262(5141):1877-1880.
Yin et al., "Delivery technologies for genome editing," Nature Reviews Drug Discovery, 2017, 16(6):387-399.
Cao et al., "Defective lymphoid development in mice lacking expression of the common cytokine receptor gamma chain," Immunity, 1995, 2(3):223-38.
Chang et al., "Modeling human severe combined immunodeficiency and correction by CRISPR/Cas9-enhanced gene targeting," Cell Reports, 2015, 12:1668-1677.
Ohbo et al., "Modulation of hematopoiesis in mice with a truncated mutant of the interleukin-2 receptor gamma chain," Blood, 1996, 87(3):956-67.
Shultz et al. "Human lymphoid and myeloid cell development in NOD/LtSz-scid IL2Rγnull mice engrafted with mobilized human hemopoietic stem cells," The Journal of Immunology, 2005,. 174(10): 6477-6489.

(Continued)

Primary Examiner — Anne Marie S Wehbe
(74) Attorney, Agent, or Firm — Fish & Richardson P.C.

(57) ABSTRACT

The present disclosure relates to the genetically modified non-human animals that have a disruption at the endogenous CD132 gene (e.g., CD132 knockout), and methods of use thereof.

7 Claims, 27 Drawing Sheets

Specification includes a Sequence Listing.

(56) References Cited

OTHER PUBLICATIONS

Zhao et al., "Construction of severe combined immunodeficiency mice based on CRISPR/Cas9 technology," Acta Laboratorium Animals Scientia Sinica, 2016, 24(4):339-343 (with English abstract only).

* cited by examiner

IMMUNODEFICIENT NON-HUMAN ANIMAL

CLAIM OF PRIORITY

This application is a continuation of and claims priority to international Application No. PCT/CN2018/079365, filed on Mar. 16, 2018, which claims the benefit of Chinese Patent Application No. 201710160547.1, filed on Mar. 17, 2017, and Chinese Patent Application No. 201810215804.1, filed on Mar. 15, 2018. The entire contents of the foregoing are incorporated herein by reference.

TECHNICAL FIELD

This disclosure relates to genetically modified animals that have a disruption at the endogenous CD132 gene (e.g., CD132 knockout), and methods of use thereof.

BACKGROUND

Immunodeficient animals are very important for disease modeling and drug developments. In recent years, immunodeficient mice are routinely used as model organisms for research of the immune system, cell transplantation strategies, and the effects of disease on mammalian systems. They have also been extensively used as hosts for normal and malignant tissue transplants, and are widely used to test the safety and efficacy of therapeutic agents.

However, the engraftment capacity of these immunodeficient animals can vary. More immunodeficient animals with different genetic makeup and better engraftment capacities are needed.

SUMMARY

This disclosure is related to genetically modified animals that have a disruption at the endogenous CD132 gene (e.g., CD132 knockout), and methods of making and use thereof.

In one aspect, the disclosure relates to a genetically-modified, non-human animal whose genome comprise a disruption in the animal's endogenous CD132 gene, wherein the disruption of the endogenous CD132 gene comprises deletion of exon 2 of the endogenous CD132 gene.

In some embodiments, the disruption of the endogenous CD132 gene further comprises deletion of exon 1 of the endogenous CD132 gene. In some embodiments, the disruption of the endogenous CD132 gene comprises deletion of part of exon 1 of the endogenous CD132 gene.

In some embodiments, the disruption of the endogenous CD132 gene further comprises deletion of one or more exons or part of exons selected from the group consisting of exon 3, exon 4, exon 5, exon 6, exon 7, and exon 8 of the endogenous CD132 gene. In some embodiments, the disruption of the endogenous CD132 gene comprises deletion of exons 1-8 of the endogenous CD132 gene.

In some embodiments, the disruption of the endogenous CD132 gene further comprises deletion of one or more introns or part of introns selected from the group consisting of intron 1, intron 2, intron 3, intron 4, intron 5, intron 6, and intron 7 of the endogenous CD132 gene.

In some embodiments, the disruption consists of deletion of more than 150 nucleotides in exon 1; deletion of the entirety of intron 1, exon 2, intron 2, exon 3, intron 3, exon 4, intron 4, exon 5, intron 5, exon 6, intron 6, exon 7, intron 7; and deletion of more than 250 nucleotides in exon 8.

In some embodiments, the animal is homozygous with respect to the disruption of the endogenous CD132 gene. In some embodiments, the animal is heterozygous with respect to the disruption of the endogenous CD132 gene.

In some embodiments, the disruption prevents the expression of functional CD132 protein.

In some embodiments, the length of the remaining exon sequences at the endogenous CD132 gene locus is less than 30% of the total length of all exon sequences of the endogenous CD132 gene. In some embodiments, the length of the remaining sequences at that the endogenous CD132 gene locus is less than 15% of the full sequence of the endogenous CD132 gene.

In another aspect, the disclosure relates to a genetically-modified, non-human animal, wherein the genome of the animal does not have exon 2 of CD132 gene at the animal's endogenous CD132 gene locus.

In some embodiments, the genome of the animal does not have one or more exons or part of exons selected from the group consisting of exon 1, exon 3, exon 4, exon 5, exon 6, exon 7, and exon 8. In some embodiments, the genome of the animal does not have one or more introns or part of introns selected from the group consisting of intron 1, intron 2, intron 3, intron 4, intron 5, intron 6, and intron 7.

In one aspect, the disclosure also provides a CD132 knockout non-human animal, wherein the genome of the animal comprises from 5' to 3' at the endogenous CD132 gene locus, (a) a first DNA sequence; optionally (b) a second DNA sequence comprising an exogenous sequence; (c) a third DNA sequence, wherein the first DNA sequence, the optional second DNA sequence, and the third DNA sequence are linked, wherein the first DNA sequence comprises an endogenous CD132 gene sequence that is located upstream of intron 1, the second DNA sequence can have a length of 0 nucleotides to 300 nucleotides, and the third DNA sequence comprises an endogenous CD132 gene sequence that is located downstream of intron 7.

In some embodiments, the first DNA sequence comprises a sequence that has a length (5' to 3') of from 10 to 100 nucleotides (e.g., approximately 10, 20, 30, 40, 50, 60, 70, 80, 90, 100 nucleotides), wherein the length of the sequence refers to the length from the first nucleotide in exon 1 of the CD132 gene to the last nucleotide of the first DNA sequence.

In some embodiments, the first DNA sequence comprises at least 10 nucleotides from exon 1 of the endogenous CD132 gene. In some embodiments, the first DNA sequence has at most 100 nucleotides from exon 1 of the endogenous CD132 gene.

In some embodiments, the third DNA sequence comprises a sequence that has a length (5' to 3') of from 200 to 600 nucleotides (e.g., approximately 200, 250, 300, 350, 400, 450, 500, 550, 600 nucleotides), wherein the length of the sequence refers to the length from the first nucleotide in the third DNA sequence to the last nucleotide in exon 8 of the endogenous CD132 gene.

In some embodiments, the third DNA sequence comprises at least 300 nucleotides from exon 8 of the endogenous CD132 gene. In some embodiments, the third DNA sequence has at most 400 nucleotides from exon 8 of the endogenous CD132 gene.

In one aspect, the disclosure also relates to a genetically-modified, non-human animal produced by a method comprising knocking out one or more exons of endogenous CD132 gene by using (1) a first nuclease comprising a zinc finger protein, a TAL-effector domain, or a single guide RNA (sgRNA) DNA-binding domain that binds to a target sequence in exon 1 of the endogenous CD132 gene or upstream of exon 1 of the endogenous CD132 gene, and (2) a second nuclease comprising a zinc finger protein, a TAL-effector domain, or a single guide RNA (sgRNA) DNA-binding domain that binds to a sequence in exon 8 of the endogenous CD132 gene.

In some embodiments, the nuclease is CRISPR associated protein 9 (Cas9). In some embodiments, the target sequence in exon 1 of the endogenous CD132 gene or upstream of exon 1 of the endogenous CD132 gene is set forth in SEQ ID NO: 1, 2, 3, or 4, and the target sequence in exon 8 of the endogenous CD132 gene is set forth in SEQ ID NO: 5, 6, 7, or 8. In some embodiments, the first nuclease comprises a sgRNA that targets SEQ ID NO: 3 and the second nuclease comprises a sgRNA that targets SEQ ID NO: 6.

In some embodiments, the animal does not express a functional CD132 protein. In some embodiments, the animal does not express a functional interleukin-2 receptor.

In some embodiments, the animal has one or more of the following characteristics:
(a) the percentage of T cells (CD3+ cells) is less than 2%, 1.5%, 1%, 0.7%, or 0.5% of leukocytes in the animal;
(b) the percentage of B cells (e.g., CD3− CD19+ cells) is less than 0.1% or 0.05% of leukocytes in the animal;
(c) the percentage of NK cells (e.g., CD3− CD49b+ cells) is less than 2% or 1.5% of leukocytes in the animal;
(d) the percentage of CD4+ T cells is less than 0.5%, 0.3%, or 0.1% of T cells;
(e) the percentage of CD8+ T cells is less than 0.5%, 0.3%, or 0.1% of T cells;
(f) the percentage of CD3+ CD4+ cells, CD3+ CD8+ cells, CD3− CD19+ cells is less than 1% or 0.5% of leukocytes in the animal;
(g) the percentage of T cells, B cells, and NK cells is less than 5%, 4%, 3%, 2% or 1% of leukocytes in the animal.

In some embodiments, the animal after being engrafted with human hematopoietic stem cells to develop a human immune system has one or more of the following characteristics:
(a) the percentage of human CD45+ cells is greater than 70% or 80% of leukocytes of the animal;
(b) the percentage of human CD3+ cells is greater than 45% of leukocytes in the animal; and
(c) the percentage of human CD19+ cells is greater than 20% or 25% of leukocytes in the animal.

In some embodiments, the animal has an enhanced engraftment capacity of exogenous cells relative to a NOD/scid mouse.

In some embodiments, the animal has one or more of the following characteristics:
(a) the animal has no functional T-cells and/or no functional B-cells;
(b) the animal exhibits reduced macrophage function relative to a NOD/scid mouse;
(c) the animal exhibits no NK cell activity; and
(d) the animal exhibits reduced dendritic function relative to a NOD/scid mouse.

In some embodiments, the animal is a mammal, e.g., a monkey, a rodent, a rat, or a mouse. In some embodiments, the animal is a NOD/scid mouse, or a NOD/scid nude mouse.

In some embodiments, the animal further comprises a sequence encoding a human or chimeric protein. In some embodiments, the human or chimeric protein is programmed cell death protein 1 (PD-1) or CD137.

In some embodiments, the animal further comprises a disruption in the animal's endogenous Beta-2-Microglobulin (B2m) gene and/or a disruption in the animal's endogenous Forkhead Box N1 (Foxn1) gene.

In another aspect, the disclosure also relates to methods of determining effectiveness of an agent or a combination of agents for the treatment of cancer. The methods involve the steps of engrafting tumor cells to the animal as described herein, thereby forming one or more tumors in the animal; administering the agent or the combination of agents to the animal; and determining the inhibitory effects on the tumors.

In some embodiments, before engrafting the tumor cells to the animal, human peripheral blood cells (hPBMC) or human hematopoietic stem cells are injected to the animal.

In some embodiments, the tumor cells are from cancer cell lines. In some embodiments, the tumor cells are from a tumor sample obtained from a human patient.

In some embodiments, the inhibitory effects are determined by measuring the tumor volume in the animal.

In some embodiments, the tumor cells are melanoma cells, lung cancer cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

In some embodiments, the agent is an anti-CD47 antibody or an anti-PD-1 antibody.

In some embodiments, the combination of agents comprises one or more agents selected from the group consisting of paclitaxel, cisplatin, carboplatin, pemetrexed, 5-FU, gemcitabine, oxaliplatin, docetaxel, and capecitabine.

In one aspect, the disclosure also provides methods of producing an animal comprising a human hemato-lymphoid system. The methods involve engrafting a population of cells comprising human hematopoietic cells or human peripheral blood cells into the animal as described herein.

In some embodiments, the human hemato-lymphoid system comprises human cells selected from the group consisting of hematopoietic stem cells, myeloid precursor cells, myeloid cells, dendritic cells, monocytes, granulocytes, neutrophils, mast cells, lymphocytes, and platelets.

In some embodiments, the methods further include the step of irradiating the animal prior to the engrafting.

In one aspect, the disclosure is also related to methods of producing a CD132 knockout mouse. The methods involve
(a) transforming a mouse embryonic stem cell with a gene editing system that targets endogenous CD132 gene, thereby producing a transformed embryonic stem cell;
(b) introducing the transformed embryonic stem cell into a mouse blastocyst;
(c) implanting the mouse blastocyst into a pseudopregnant female mouse; and
(d) allowing the blastocyst to undergo fetal development to term, thereby obtaining the CD132 knockout mouse.

In another aspect, the disclosure also provides methods of producing a CD132 knockout mouse. The methods include the steps of
(a) transforming a mouse embryonic stem cell with a gene editing system that targets endogenous CD132 gene, thereby producing a transformed embryonic stem cell;
(b) implanting the transformed embryonic cell into a pseudopregnant female mouse; and
(c) allowing the transformed embryonic cell to undergo fetal development to term, thereby obtaining the CD132 knockout mouse.

In some embodiments, the gene editing system comprises a first nuclease comprising a zinc finger protein, a TAL-effector domain, or a single guide RNA (sgRNA) DNA-binding domain that binds to a target sequence in exon 1 of the endogenous CD132 gene or upstream of exon 1 of the endogenous CD132 gene, and a second nuclease comprising a zinc finger protein, a TAL-effector domain, or a single guide RNA (sgRNA) DNA-binding domain that binds to a sequence in exon 8 of the endogenous CD132 gene.

In some embodiments, the nuclease is CRISPR associated protein 9 (Cas9).

In some embodiments, the target sequence in exon 1 of the endogenous CD132 gene or upstream of exon 1 of the endogenous CD132 gene is set forth in SEQ ID NO: 1, 2, 3, or 4, and the target sequence in exon 8 of the endogenous CD132 gene is set forth in SEQ ID NO: 5, 6, 7, or 8.

In some embodiments, the mouse embryonic stem cell has a NOD/scid background, or a NOD/scid nude background.

In some embodiments, the mouse embryonic stem cell comprises a sequence encoding a human or chimeric protein. In some embodiments, the human or chimeric protein is PD-1 or CD137.

In some embodiments, the mouse embryonic stem cell has a genome comprising a disruption in the animal's endogenous Beta-2-Microglobulin (B2m) gene and/or a disruption in the animal's endogenous Forkhead Box N1 (Foxn1) gene.

In another aspect, the disclosure relates to a non-human mammalian cell, comprising a disruption, a deletion, or a genetic modification as described herein.

In some embodiments, the cell includes Cas9 mRNA or an in vitro transcript thereof.

In some embodiments, the non-human mammalian cell is a mouse cell. In some embodiments, the cell is a fertilized egg cell. In some embodiments, the cell is a germ cell. In some embodiments, the cell is a blastocyst.

In another aspect, the disclosure relates to methods for establishing a CD132 knockout animal model. The methods include the steps of:

(a) providing the cell with a disruption in the endogenous CD132 gene, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring of the pregnant female in step (c).

In some embodiments, the establishment of a CD132 knockout animal involves a gene editing technique that is based on CRISPR/Cas9.

In some embodiments, the non-human mammal is mouse. In some embodiments, the non-human mammal in step (c) is a female with false pregnancy.

In another aspect, the disclosure relates to a tumor bearing non-human mammal model, characterized in that the non-human mammal model is obtained through the methods as described herein.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD132 gene function, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
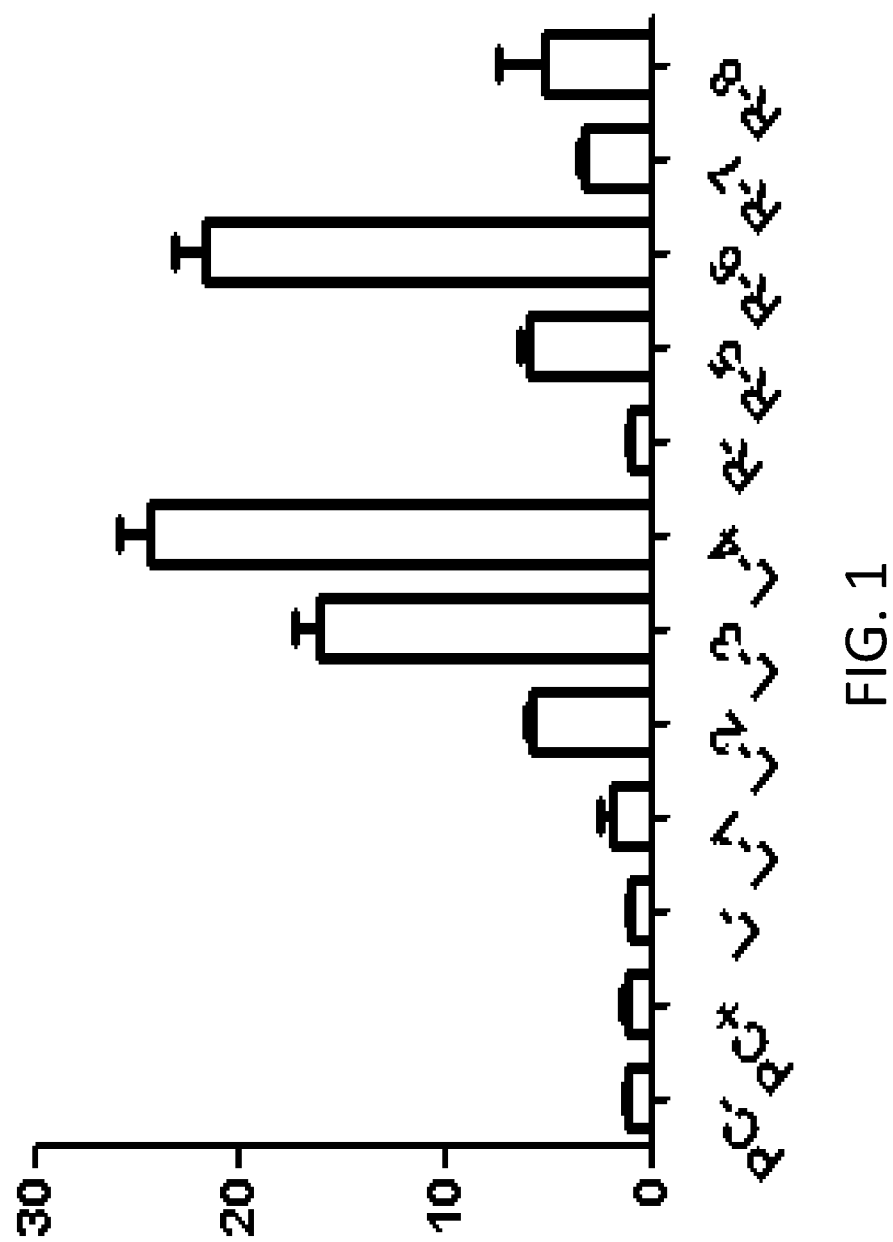
FIG. 1 is a graph showing activity testing results for sgRNA1-sgRNA8 (PC– is a negative control; PC+ is a positive control; L– is a negative control for 5' target sequence; R– is a negative control for 3' target sequence; L-1 to L-4 correspond to sgRNA-1 to sgRNA-4; R-5 to R-8 correspond to sgRNA-5 to sgRNA-8).

This disclosure relates to CD132 knockout non-human animals, and methods of use thereof.

CD132, also known as interleukin-2 receptor subunit gamma or IL2RG, is a cytokine receptor sub-unit that is common to the receptor complexes for IL-2, IL-4, IL-7, IL-9, IL-15 and IL-21. These receptors are members of the type I cytokine receptor family expressed on most lymphocyte populations.

CD132 is located on the surface of immature blood-forming cells in bone marrow. One end of the protein resides outside the cell where it binds to cytokines and the other end of the protein resides in the interior of the cell where it transmits signals to the cell's nucleus. The common gamma chain partners with other proteins to direct blood-forming cells to form lymphocytes. The receptor also directs the growth and maturation of lymphocyte subtypes: T cells, B cells, and natural killer cells.

The present disclose provides CD132 knockout non-human animals, which can be used as a research tool for studying the etiology, pathogenesis of various diseases, as well as the development of therapeutic drugs for various diseases (e.g., cancers).

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD132 (Interleukin-2 Receptor Subunit Gamma or IL2RG)

Interleukin-2 (IL-2) is a 15.5 kDa type 1 four α-helical bundle cytokine produced primarily by CD4+ T cells following their activation by antigen. IL-2 was the first type 1 cytokine cloned and the first cytokine for which a receptor component was cloned. Three different IL-2 receptor chains exist that together generate low, intermediate, and high affinity IL-2 receptors. The ligand-specific IL-2 receptor α chain (IL-2Rα, CD25, Tac antigen), which is expressed on activated but not non-activated lymphocytes, binds IL-2 with low affinity (Kd~$10^{-8}$ M); the combination of IL-2Rβ (CD122) and IL-2Rγ (CD132) together form an IL-2Rβ/γc complex mainly on memory T cells and NK cells that binds IL-2 with intermediate affinity (Kd~$10^{-9}$ M); and when all three receptor chains are co-expressed on activated T cells and Treg cells, IL-2 is bound with high affinity (Kd~$10^{-11}$ M).

For the high affinity receptor, the three dimensional structure of the quaternary complex supports a model wherein IL-2 initially bind IL-2Rα, then IL-2Rβ is recruited, and finally IL-2Rγ. The intermediate and high affinity receptor forms are functional, transducing IL-2 signals.

CD132 is also an essential component shared by the receptors for IL-2, IL-4, IL-7, IL-9, IL-15, and IL-21.

IL-2Rγ is encoded by the gene, IL2RG (CD132), that is mutated in humans with X-linked severe combined immunodeficiency (XSCID) and physically recruits JAK3, which when mutated also causes an XSCID-like T-B+NK− form of SCID. In XSCID and JAK3-deficient SCID, the lack of signaling by IL-7 and IL-15, respectively, explains the lack of T and NK cell development, whereas defective signaling by IL-4 and IL-21 together explain the non-functional B cells and hypogammaglobulinemia.

A detailed description of CD132 and its function can be found, e.g., in Liao et al. "IL-2 family cytokines: new insights into the complex roles of IL-2 as a broad regulator of T helper cell differentiation," Current opinion in immunology 23.5 (2011): 598-604; Noguchi et al. "Interleukin-2 receptor gamma chain: a functional component of the interleukin-7 receptor," Science 262.5141 (1993): 1877-1880; Henthorn et al. "IL-2Rγ gene microdeletion demonstrates that canine X-linked severe combined immunodeficiency is a homologue of the human disease," Genomics 23.1 (1994): 69-74; and U.S. Pat. No. 7,145,055; each of which is incorporated herein by reference in its entirety.

In human genomes, CD132 gene (Gene ID: 3561) is located on X chromosome, and has eight exons, exon 1, exon 2, exon 3, exon 4, exon 5, exon 6, exon 7, and exon 8. The CD132 protein also has an extracellular region, a transmembrane region, and a cytoplasmic region. The nucleotide sequence for human CD132 mRNA is NM_000206.2, and the amino acid sequence for human CD132 is NP_000197.1.

Figure 27:
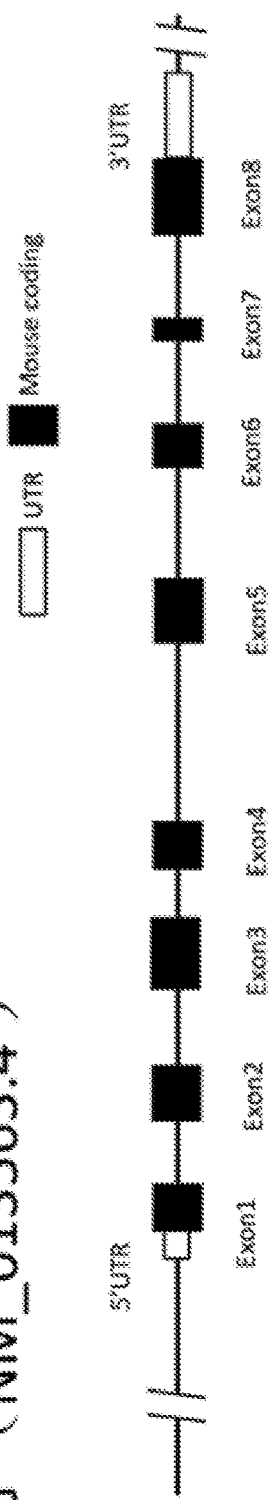
FIG. 27 is a diagram showing the mouse CD132 (IL2RG) locus.

Similarly, in mice, CD132 gene locus has eight exons, exon 1, exon 2, exon 3, exon 4, exon 5, exon 6, exon 7, and exon 8 (FIG. 27). The CD132 protein also has an extracellular region, a transmembrane region, and a cytoplasmic region, and the signal peptide is located at the extracellular region of CD132. The nucleotide sequence for mouse CD132 cDNA is NM_013563.4 (SEQ ID NO: 18), the amino acid sequence for mouse CD132 is NP_038591.1 (SEQ ID NO: 19). The location for each exon and each region in the mouse CD132 nucleotide sequence and amino acid sequence is listed below:

TABLE 1

| Mouse CD132 (approximate location) | NM_013563.4 1663bp | NP_038591.1 369aa |
|---|---|---|
| Exon 1 | 1-201 | 1-38 |
| Exon 2 | 202-355 | 39-90 |
| Exon 3 | 356-540 | 91-151 |
| Exon 4 | 541-683 | 152-199 |
| Exon 5 | 684-846 | 200-253 |
| Exon 6 | 847-943 | 254-286 |
| Exon 7 | 944-1010 | 287-308 |
| Exon 8 | 1011-1663 | 309-369 |
| Signal peptide | 87-158 | 1-24 |
| Extracellular region (excluding signal peptide region) | 159-875 | 25-263 |
| Transmembrane region | 876-938 | 264-284 |
| Cytoplasmic region | 939-1193 | 285-369 |

The mouse CD132 gene (Gene ID: 16186) is located in Chromosome X of the mouse genome, which is located from 101,268,255 to 101,264,385 of NC_000086.7 (GRCm38.p4 (GCF_000001635.24)). The 5'-UTR is from 101,268,255 to 101,268,170, exon 1 is from 101,268,255 to 101,268,055, the first intron (intron 1) is from 101,268,054 to 101,267,865, exon 2 is from 101,267,864 to 101,267,711, the second intron (intron 2) is from 101,267,710 to 101,267,496, exon 3 is from 101,267,495 to 101,267,311, the third intron (intron 3) is from 101,267,310 to 101,267,121, exon 4 is from 101,267,120 to 101,266,978, the fourth intron (intron 4) is from 101,266,977 to 101,266,344, exon 5 is from 101,266,343 to 101,266,181, the fifth intron (intron 5) is from 101,266,180 to 101,265,727, exon 6 is from 101,265,726 to 101,265,630, the sixth intron (intron 6) is from 101,265,629 to 101,265,443, exon 7 is from 101,265,442 to 101,265,376, the seventh intron (intron 7) is from 101,265,375 to 101,265,038, exon 8 is from 101,265,037 to 101,264,378, and the 3'-UTR is from 101,264,851 to 101,264,378, based on transcript NM 013563.4. All relevant information for mouse CD132 locus can be found in the NCBI website with Gene ID: 16186, which is incorporated by reference herein in its entirety.

CD132 genes, proteins, and locus of the other species are also known in the art. For example, the gene ID for CD132 in Rattus norvegicus is 140924, the gene ID for CD132 in Macaca mulatta (Rhesus monkey) is 641338, the gene ID for CD132 in *Sus scrofa* (pig) is 397156. The relevant information for these genes (e.g., intron sequences, exon sequences, amino acid residues of these proteins) can be found, e.g., in NCBI database.

The present disclosure provides a genetically-modified, non-human animal whose genome comprise a disruption in the animal's endogenous CD132 gene, wherein the disruption of the endogenous CD132 gene comprises deletion of one or more exons, or part of the one or more exons, wherein the one or more exons are selected from the group consisting of exon 1, exon 2, exon 3, exon 4, exon 5, exon 6, exon 7, and exon 8 of the endogenous CD132 gene. Thus, the disclosure provides a genetically-modified, non-human animal that does not have one or more exons that are selected from the group consisting of exon 1, exon 2, exon 3, exon 4, exon 5, exon 6, exon 7, and exon 8 of the endogenous CD132 gene.

As used herein, the term "deletion of an exon" refers to the deletion the entire exon. For example, deletion of exon 2 means that all sequences in exon 2 are deleted.

As used herein, the term "deletion of part of an exon" refers to at least one nucleotide, but not all nucleotides in the exon is deleted. In some embodiment, at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleotides in the exon are deleted.

In some embodiments, the disruption comprises deletion of one or more introns, or part of the one or more introns, wherein the one or more introns are selected from the group consisting of intron 1, intron 2, intron 3, intron 4, intron 5, intron 6, and intron 7 of the endogenous CD132 gene. Thus, the disclosure provides a genetically-modified, non-human animal does not have one or more introns that are selected from the group consisting of intron 1, intron 2, intron 3, intron 4, intron 5, intron 6, and intron 7 of the endogenous CD132 gene.

In some embodiments, the disruption of the endogenous CD132 gene comprises deletion of exon 2 of the endogenous CD132 gene. In some embodiments, the disruption of the endogenous CD132 gene further comprises deletion of exon 1, or part of exon 1 of the endogenous CD132 gene.

In some embodiments, the entire sequence of mouse exon 1, exon 2, exon 3, exon 4, exon 5, exon 6, exon 7, and exon 8 are deleted. In some embodiments, the signal peptide region, extracellular region, transmembrane region, and/or cytoplasmic region of CD132 are deleted.

In some embodiments, a "region" or "portion" of mouse exon 1, exon 2, exon 3, exon 4, exon 5, exon 6, exon 7, exon 8, intron 1, intron 2, intron 3, intron 4, intron 5, intron 6, and intron 7, signal peptide region, extracellular region, transmembrane region, and/or cytoplasmic region are deleted. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides.

In some embodiments, the "region" or "portion" can be at least 10%, 20%, 30%, 40%, 50%, 55%, 60%, 65%, 70%, 75%, 80%, 85%, 90%, 95%, or 99% of exon 1, exon 2, exon 3, exon 4, exon 5, exon 6, exon 7, exon 8, intron 1, intron 2, intron 3, intron 4, intron 5, intron 6, and intron 7, signal peptide region, extracellular region, transmembrane region, or cytoplasmic region. In some embodiments, a region, a portion, or the entire sequence of mouse exon 1, exon 2, exon 3, exon 4, exon 5, exon 6, exon 7, and/or exon 8 are deleted. In some embodiments, a region, a portion, or the entire sequence of mouse intron 1, intron 2, intron 3, intron 4, intron 5, intron 6, and/or intron 7 are deleted.

In some embodiments, the disruption comprises or consists of deletion of more than 100, 110, 120, 130, 140, 150, 160, 170, 180, 190, 200, 250, 300, 350, 400, 450, 500, 550, 600, or 650 nucleotides in exon 1, exon 2, exon 3, exon 4, exon 5, exon 6, exon 7, and/or exon 8. In some embodiments, the disruption comprises or consists of deletion of more than 100, 110, 120, 130, 140, 150, 160, 170, 180, 190, 200, 250, 300, 350, 400, 450, 500, 550, 600, 650, 700, 800, 900, or 1000 nucleotides in intron 1, intron 2, intron 3, intron 4, intron 5, intron 6, and/or intron 7.

In some embodiments, the disruption comprises or consists of deletion of more than 100, 110, 120, 130, 140, 150, 160, 170, 180, 190, or 200 nucleotides (e.g., about 150 or 160 nucleotides) in exon 1; deletion of the entirety of intron 1, exon 2, intron 2, exon 3, intron 3, exon 4, intron 4, exon 5, intron 5, exon 6, intron 6, exon 7, intron 7; and/or deletion of more than 100, 110, 120, 130, 140, 150, 160, 170, 180, 190, 200, 210, 220, 230, 240, 250, 260, 270, 280, 290, 300, 350, 400, 450, 500, 550, 600, or 650 nucleotides (e.g., about 200, 250 or 270 nucleotides) in exon 8.

In some embodiments, the length of the remaining exon sequences at the endogenous CD132 gene locus is less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50% of the total length of all exon sequences of the endogenous CD132 gene. In some embodiments, the length of the remaining exon sequences at the endogenous CD132 gene locus is more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50% of the total length of all exon sequences of the endogenous CD132 gene.

In some embodiments, the length of the remaining sequences at that the endogenous CD132 gene locus is less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50% of the full sequence of the endogenous CD132 gene. In some embodiments, the length of the remaining sequences at that the endogenous CD132 gene locus is more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50% of the full sequence of the endogenous CD132 gene.

The present disclosure further relates to the genomic DNA sequence of a CD132 knockout mouse. In some embodiments, the genome of the animal comprises from 5' to 3' at the endogenous CD132 gene locus, (a) a first DNA sequence; optionally; (b) a second DNA sequence comprising an exogenous sequence; (c) a third DNA sequence, wherein the first DNA sequence, the optional second DNA sequence, and the third DNA sequence are linked.

The second DNA sequence can have a length of 0 nucleotides to 300 nucleotides (e.g., about 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290 or 300 nucleotides). In some embodiments, the second DNA sequence has only 0 nucleotides, which means that there is no extra sequence between the first DNA sequence and the third DNA sequence. In some embodiments, the second DNA sequence has at least 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290 or 300 nucleotides. In some embodiments, the second DNA sequence has at most 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290 or 300 nucleotides.

In some embodiments, the first DNA sequence comprises an endogenous CD132 gene sequence that is located upstream of intron 1, and can include all or just part of sequences that is located upstream of intron 1. In some embodiments, the first DNA sequence comprises an endogenous CD132 gene sequence that is located upstream of exon 1. In some embodiments, the first DNA sequence comprises a sequence that has a length (5' to 3') of from 10 to 200 nucleotides (e.g., from 10 to 100 nucleotides, or from 10 to 20 nucleotides) starting from the first nucleotide in exon 1 of the CD132 gene to the last nucleotide of the first DNA sequence. In some embodiments, the first DNA sequence comprises at least 5, 10, 11, 12, 13, 14, 15, 16, 17, 18, 19, 20, 30, 40, or 50, 60, 70, 80, 90, 100, 110, 120, 130, 140, 150, 160, 170, 180, 190, or 200 nucleotides from exon 1. In some embodiments, the first DNA sequence has at most 5, 10, 11, 12, 13, 14, 15, 16, 17, 18, 19, 20, 30, 40, or 50, 60, 70, 80, 90, 100, 110, 120, 130, 140, 150, 160, 170, 180, 190, or 200 nucleotides from exon 1.

In some embodiments, the third DNA sequence comprises an endogenous CD132 gene sequence that is located downstream of the last intron (e.g., intron 7 in mouse), and can include all or just part of sequences that is located downstream of intron 7. In some embodiments, the third DNA sequence comprises a sequence that has a length (5' to 3') of from 200 to 600 nucleotides (e.g., from 300 to 400 nucleotides, or from 350 to 400 nucleotides) starting from the first nucleotide in the third DNA sequence to the last nucleotide in the last exon (e.g., exon 8 in mouse) of the endogenous CD132 gene. In some embodiments, the third DNA sequence comprises at least 100, 150, 200, 250, 300, 350, 400, 450, 500, 550, 600, or 650 nucleotides from the last exon (e.g., exon 8 in mouse). In some embodiments, the third DNA sequence has at most 100, 150, 200, 250, 300, 350, 400, 450, 500, 550, 600, or 650 nucleotides from the last exon (e.g., exon 8 in mouse).

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein (e.g., exon sequences, intron sequences, the remaining exon sequences, the deleted sequences), and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein (e.g., amino acid sequences encoded by exons). In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

Cells, tissues, and animals (e.g., mouse) are also provided that comprise a disruption of the endogenous CD132 gene as described herein, as well as cells, tissues, and animals (e.g., mouse) that have any nucleic acid sequence as described herein.

Genetically Modified Animals

As used herein, the term "genetically-modified non-human animal" refers to a non-human animal having a modified sequence (e.g., deletion of endogenous sequence or insertion of exogenous sequence) in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the modified sequence in its genome. The cell having the modified sequence can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a disruption or a deletion at the endogenous CD132 locus. The animals are generally able to pass the modification to progeny, i.e., through germline transmission.

In some embodiments, the genetically-modified non-human animal does not express CD132 (e.g., intact or functional CD132 protein). Because CD132 is a cytokine receptor sub-unit that is common to the receptor complexes for IL-2, IL-4, IL-7, IL-9, IL-15 and IL-21, the genetically-modified non-human animal does not have functional IL-2, IL-4, IL-7, IL-9, IL-15 and/or IL-21.

Furthermore, because IL-7 and IL-15 are important for T and NK cell development, and IL-4 and IL-21 are important for B cell development, in some embodiments, the genetically-modified non-human animal lack functional T cells, B cells, and/or NK cells.

Thus, in some embodiments, the animal can have one or more of the following characteristics:

(a) the percentage of T cells (CD3+ cells) is less than 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2% or 0.1% of leukocytes in the animal;

(b) the percentage of B cells (e.g., CD3− CD19+ cells) is less than 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02% or 0.01% of leukocytes in the animal;

(c) the percentage of NK cells (e.g., CD3− CD49b+ cells) is less than 2%, 1.9%, 1.8%, 1.7%, 1.6%, 1.5%, 1.4%, 1.3%, 1.2%, 1.1%, 1%, 0.9%, 0.8%, 0.7%, 0.6%, or 0.5% of leukocytes in the animal;

(d) the percentage of CD4+ T cells (CD3+ CD4+ cells) is less than 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of T cells;

(e) the percentage of CD8+ T cells (CD3+ CD8+ cells) is less than 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of T cells;

(f) the percentage of CD3+ CD4+ cells, CD3+ CD8+ cells, CD3− CD19+ cells is less than 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of leukocytes in the animal;

(g) the percentage of T cells (CD3+ cells) and NK cells (CD3− CD49b+ cells) is less than 5%, 4%, 3%, 2%, 1%, 0.9%, 0.8%, 0.7%, 0.6%, 0.5%, 0.4%, 0.3%, 0.2%, or 0.1% of leukocytes in the animal.

As used herein, the term "leukocytes" or "white blood cells" include neutrophils, eosinophils (acidophilus), basophils, lymphocytes, and monocytes. All leukocytes have nuclei, which distinguishes them from the anucleated red blood cells (RBCs) and platelets. CD45, also known as leukocyte common antigen (LCA), is a cell surface marker for leukocytes. Among leukocytes, monocytes and neutrophils are phagocytic.

Lymphocytes is a subtype of leukocytes. Lymphocytes include natural killer (NK) cells (which function in cell-mediated, cytotoxic innate immunity), T cells, and B cells.

In some embodiments, the variations among individual B-NDG mice are very small. In some embodiments, the standard deviations of the percentages are less than 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02% or 0.01%.

In some embodiments, the genetically-modified non-human animal is a mouse.

The genetically-modified mouse can also have one or more of the following characteristics:

(a) the genetically-modified mouse has no functional T-cells and/or no functional B-cells;

(b) the genetically-modified mouse exhibits reduced macrophage function relative to a NOD/scid mouse, or a NOD/scid nude mouse;

(c) the genetically-modified mouse exhibits no NK cell activity;

(d) the genetically-modified mouse exhibits reduced dendritic function relative to a NOD/scid mouse, or a NOD/scid nude mouse; and (e) the genetically-modified mouse has an enhanced engraftment capacity of exogenous cells relative to a NOD/scid mouse, or a NOD/scid nude mouse.

The genetically modified non-human animal can also be various other animals, e.g., a rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the CD132 knockout animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes).

Non-limiting examples of such mice include, e.g., NOD mice, SCID mice, NOD/SCID mice, nude mice, NOD/SCID nude mice, and Rag1 and/or Rag2 knockout mice. These mice can optionally be irradiated, or otherwise treated to destroy one or more immune cell type. Thus, in various embodiments, a genetically modified mouse is provided that can include a disruption of the endogenous non-human CD132 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, nude mice, Rag1 and/or Rag2 knockout mice, and a combination thereof. These genetically modified animals are described, e.g., in US20150106961, which is incorporated herein by reference in its entirety.

Although genetically modified cells are also provided that can comprise the modifications (e.g., disruption) described herein (e.g., ES cells, somatic cells), in many embodiments, the genetically modified non-human animals comprise the modification of the endogenous CD132 locus in the germline of the animal.

Furthermore, the genetically modified animal can be homozygous with respect to the disruption of the endogenous CD132 gene. In some embodiments, the animal can be heterozygous with respect to the disruption of the endogenous CD132 gene.

The present disclosure further relates to a non-human mammal generated through the methods as described herein. In some embodiments, the genome thereof contains human gene(s).

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains a disruption of the CD132 gene in the genome of the animal.

Genetic, molecular and behavioral analyses for the non-human mammals described above can be performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The disruption of CD132 gene can be detected by a variety of methods.

There are also many analytical methods that can be used to detect DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). Many standard analysis methods can be used to complete quantitative measurements. For example, transcription levels of wildtype CD132 can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human proteins.

Vectors

The disclosure also provides vectors for constructing a CD132 animal model. In some embodiments, the vectors comprise sgRNA sequence, wherein the sgRNA sequence target CD132 gene, and the sgRNA is unique on the target sequence of the CD132 gene to be altered, and meets the sequence arrangement rule of 5'-NNN(20)-NGG3' or 5'-CCN—N(20)-3'; and in some embodiments, the targeting site of the sgRNA in the mouse CD132 gene is located on the exon 1, exon 2, exon 3, exon 4, exon 5, exon 6, exon 7, exon 8, intron 1, intron 2, intron 3, intron 4, intron 5, intron 6, and intron 7, upstream of exon 1, or downstream of exon8 of the mouse CD132 gene.

In some embodiments, the 5' targeting sequence for the knockout sequence is shown as SEQ ID NOS: 1-4, and the sgRNA sequence recognizes the 5' targeting site. In some embodiments, the 3' targeting sequence for the knockout sequence is shown as SEQ ID NOS: 5-8 and the sgRNA sequence recognizes the 3' targeting site.

Thus, the disclosure provides sgRNA sequences for constructing a CD132 knockout animal model. In some embodiments, the oligonucleotide sgRNA sequences are set forth in SEQ ID NOS: 9-12.

In some embodiments, the disclosure relates to a plasmid construct (e.g., pT7-sgRNA) including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR- Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides knocking out in at least one cell of the animal, at an endogenous CD132 gene locus, one or more exons (e.g., 1, 2, 3, 4, 5, 6, 7, or 8 exons) and/or one or more introns (e.g., 1, 2, 3, 4, 5, 6, or 7 introns) of the endogenous CD132 gene. In some embodiments, the modification occurs in a germ cell, a somatic cell, a blastocyst, or a fibroblast, etc. The nucleus of a somatic cell or the fibroblast can also be inserted into an enucleated oocyte.

In some embodiments, cleavages at the upstream and the downstream of the knockout sequence by a nuclease (e.g., by zinc finger nucleases, TALEN or CRISPR) can result in DNA double strands break, and non-homologous end joining (NHEJ) occurs and ligates the break ends, thereby knocking out the sequence of interest. NHEJ typically utilizes short homologous DNA sequences called microhomologies to guide repair. These microhomologies are often present in single-stranded overhangs on the ends of double-strand breaks. When the overhangs are perfectly compatible, NHEJ usually repairs the break accurately. When the break ends located at the upstream and the downstream of the target sequence are ligated, imprecise repair occurs, and in some cases, leading to loss of nucleotides or insertion of random nucleotides.

Zinc finger proteins, TAL-effector domains, or single guide RNA (sgRNA) DNA-binding domains can be designed to target the upstream and the downstream of the knockout sequence. SEQ ID NOs: 1-8 are exemplary target sequences for the modification. Among them, SEQ ID NOs: 1, 2, and 4 are located at the upstream of exon 1 of mouse endogenous CD132 gene. SEQ ID NO: 3 is located on exon 1. SEQ ID NOs: 5-8 are located on exon 8. After the zinc finger proteins, TAL-effector domains, or single guide RNA (sgRNA) DNA-binding domains bind to the target sequences, the nuclease cleaves the genomic DNA, and triggers NHEJ. In some embodiments, the nuclease is CRISPR associated protein 9 (Cas9).

Thus, the methods of producing a CD132 knockout mouse can involve one or more of the following steps: transforming a mouse embryonic stem cell with a gene editing system that targets endogenous CD132 gene, thereby producing a transformed embryonic stem cell; introducing the transformed embryonic stem cell into a mouse blastocyst; implanting the mouse blastocyst into a pseudopregnant female mouse; and allowing the blastocyst to undergo fetal development to term.

In some embodiments, the transformed embryonic cell is directly implanted into a pseudopregnant female mouse instead, and the embryonic cell undergoes fetal development.

In some embodiments, the gene editing system can involve Zinc finger proteins, TAL-effector domains, or single guide RNA (sgRNA) DNA-binding domains.

The present disclosure further provides a method for establishing a CD132 gene knockout animal model, involving the following steps:

(a) providing the cell (e.g. a fertilized egg cell) with the genetic modification based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, the non-human mammal in the foregoing method is a mouse (e.g., a C57BL/6 mouse, a NOD/scid mouse, or a NOD/scid nude mouse). In some embodiments, the non-human mammal is a NOD/scid mouse. In the NOD/scid mouse, the SCID mutation has been transferred onto a non-obese diabetic (NOD) background. Animals homozygous for the SCID mutation have impaired T and B cell lymphocyte development. The NOD background additionally results in deficient natural killer (NK) cell function. In some embodiments, the non-human mammal is a NOD/scid nude mouse. The NOD/scid nude mouse additionally has a disruption of FOXN1 gene on chromosome 11 in mice.

In some embodiments, the fertilized eggs for the methods described above are NOD/scid fertilized eggs or NOD/scid nude fertilized eggs. Other fertilized eggs that can also be used in the methods as described herein include, but are not limited to, C57BL/6 fertilized eggs, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

The genetically modified animals (e.g., mice) as described herein can have several advantages. For example, the genetically modified mice do not require backcrossing, and thus have a relatively purer background (e.g., NOD/scid) as compared to some other immunodeficient mice known in the art. A pure background is beneficial to obtain consistent experiment results. Furthermore, because almost all sequences in CD132 have been knocked out, these mice are likely to have a higher degree of immunodeficiency and are likely to be better recipients for engraftment as compared to some other immunodeficient mice known in the art. Despite the immunodeficiency, these mice are also relatively healthy, and have a relatively long life span (e.g., more than 1 year, 1.5 years, or 2 years).

Methods of Using Genetically Modified Animals

Genetically modified animals with a disruption at endogenous CD132 gene can provide a variety of uses that include, but are not limited to, establishing a human hemato-lymphoid animal model, developing therapeutics for human diseases and disorders, and assessing the efficacy of these therapeutics in the animal models.

In some embodiments, the genetically modified animals can be used for establishing a human hemato-lymphoid system. The methods involve engrafting a population of cells comprising human hematopoietic cells (CD34+ cells) or human peripheral blood cells into the genetically modified animal described herein. In some embodiments, the methods further include the step of irradiating the animal prior to the engrafting. The human hemato-lymphoid system in the genetically modified animals can include various human cells, e.g., hematopoietic stem cells, myeloid precursor cells, myeloid cells, dendritic cells, monocytes, granulocytes, neutrophils, mast cells, lymphocytes, and platelets.

The genetically modified animals described herein (e.g., with deletion of part of exon 1, deletion of exons 2-7, and deletion of part exon 8) are also an excellent animal model for establishing the human hemato-lymphoid system. In some embodiments, the animal after being engrafted with human hematopoietic stem cells or human peripheral blood cells to develop a human immune system has one or more of the following characteristics:

(a) the percentage of human CD45+ cells is greater than 50%, 55%, 65% 70%, 75%, 80%, 85%, or 90% of leukocytes or CD45+ cells of the animal;

(b) the percentage of human CD3+ cells is greater than 35%, 40%, 45%, 50%, 55%, or 60% of leukocytes or CD45+ cells in the animal; and (c) the percentage of human CD19+ cells is greater than 15%, 20%, 25%, or 30% of leukocytes or CD45+ cells in the animal.

The genetically modified animals described herein specifically does not include NSG mice or NOG mice, and in some embodiments, are better animal models for establishing the human hemato-lymphoid system (e.g., having a higher percentage of human leukocytes, human T cells, human B cells, or human NK cells). A detailed description of the NSG mice and NOD mice can be found, e.g., in Ishikawa et al. "Development of functional human blood and immune systems in NOD/SCID/IL2 receptor γ chainnull mice." Blood 106.5 (2005): 1565-1573; Katano et al. "NOD-Rag2null IL-2Rγnull mice: an alternative to NOG mice for generation of humanized mice." Experimental animals 63.3 (2014): 321-330, both of which are incorporated herein by reference in the entirety.

In some embodiments, the genetically modified animals can be used to determine the effectiveness of an agent or a combination of agents for the treatment of cancer. The methods involve engrafting tumor cells to the animal as described herein, administering the agent or the combination of agents to the animal; and determining the inhibitory effects on the tumors.

In some embodiments, the tumor cells are from a tumor sample obtained from a human patient. These animal models are also known as Patient derived xenografts (PDX) models. PDX models are often used to create an environment that resembles the natural growth of cancer, for the study of cancer progression and treatment. Within PDX models, patient tumor samples grow in physiologically-relevant tumor microenvironments that mimic the oxygen, nutrient, and hormone levels that are found in the patient's primary tumor site. Furthermore, implanted tumor tissue maintains the genetic and epigenetic abnormalities found in the patient and the xenograft tissue can be excised from the patient to include the surrounding human stroma. As a result, PDX models can often exhibit similar responses to anti-cancer agents as seen in the actual patient who provide the tumor sample.

While the genetically modified animals do not have functional T cells or B cells, the genetically modified animals still have functional phagocytic cells, e.g., neutrophils, eosinophils (acidophilus), basophils, or monocytes. Macrophages can be derived from monocytes, and can engulf and digest cellular debris, foreign substances, microbes, cancer cells. Thus, the genetically modified animals described herein can be used to determine the effect of an agent (e.g., anti-CD47 antibodies or anti-SIRPa antibodies) on phagocytosis, and the effects of the agent to inhibit the growth of tumor cells.

In some embodiments, human peripheral blood cells (hPBMC) or human hematopoietic stem cells are injected to the animal to develop human hematopoietic system. The genetically modified animals described herein can be used to determine the effect of an agent in human hematopoietic system, and the effects of the agent to inhibit tumor cell growth or tumor growth. Thus, in some embodiments, the methods as described herein are also designed to determine the effects of the agent on human immune cells (e.g., human T cells, B cells, or NK cells), e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

In some embodiments, the tested agent or the combination of tested agents is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the tested agent is designed for the treating melanoma, primary lung carcinoma, non-small cell lung carcinoma (NSCLC), small cell lung cancer (SCLC), primary gastric carcinoma, bladder cancer, breast cancer, and/or prostate cancer.

In some embodiments, the injected tumor cells are human tumor cells. In some embodiments, the injected tumor cells are melanoma cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

The inhibitory effects on tumors can also be determined by any methods known in the art. In some embodiments, the tumor cells can be labeled by a luciferase gene. Thus, the number of the tumor cells or the size of the tumor in the animal can be determined by an in vivo imaging system (e.g., the intensity of fluorescence). In some embodiments, the inhibitory effects on tumors can also be determined by measuring the tumor volume in the animal, and/or determining tumor (volume) inhibition rate ($TGI_{TV}$). The tumor growth inhibition rate can be calculated using the formula $TGI_{TV}(\%)=(1-TVt/TVc)\times 100$, where TVt and TVc are the mean tumor volume (or weight) of treated and control groups.

In some embodiments, the tested agent can be one or more agents selected from the group consisting of paclitaxel, cisplatin, carboplatin, pemetrexed, 5-FU, gemcitabine, oxaliplatin, docetaxel, and capecitabine.

In some embodiments, the tested agent can be an antibody, for example, an antibody that binds to CD47, PD-1, CTLA-4, LAG-3, TIM-3, BTLA, PD-L1, 4-1BB, CD27, CD28, CD47, TIGIT, CD27, GITR, or OX40. In some embodiments, the antibody is a human antibody.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

CD132 Knockout Animal Model with Additional Genetic Modifications

The present disclosure further relates to methods for generating genetically modified animal models described herein with some additional modifications (e.g., human or chimeric genes or additional gene knockout).

In some embodiments, the animal can comprise a disruption at the endogenous CD132 gene and a sequence encoding a human or chimeric protein. In some embodiments, the human or chimeric protein can be programmed cell death protein 1 (PD-1), TNF Receptor Superfamily Member 9 (4-1BB or CD137), cytotoxic T-lymphocyte-associated protein 4 (CTLA-4), LAG-3, T-cell immunoglobulin and mucin-domain containing-3 (TIM-3), B And T Lymphocyte Associated (BTLA), Programmed Cell Death 1 Ligand 1 (PD-L1), CD27, CD28, CD47, T-Cell Immunoreceptor With Ig And ITIM Domains (TIGIT), Glucocorticoid-Induced TNFR-Related Protein (GITR), or TNF Receptor Superfamily Member 4 (TNFRSF4; or OX40).

In some embodiments, the animal can comprise a disruption at the endogenous CD132 gene and a disruption at some other endogenous genes (e.g., Beta-2-Microglobulin (B2m) or Forkhead Box N1 (Foxn1)).

The methods of CD132 knockout animal model with additional genetic modifications (e.g., humanized genes or additional gene knockout) can include the following steps:

(a) using the methods as described herein to obtain a CD132 knockout animal;

(b) mating the CD132 knockout animal with another genetically modified non-human animal with the desired genetic modifications, and then screening the progeny to obtain a CD132 animal with the desired genetic modifications.

In some embodiments, in step (b) of the method, the genetically modified animal can be mated with a genetically modified non-human animal with human or chimeric PD-1, CTLA-4, LAG-3, TIM-3, BTLA, PD-L1, 4-1BB, CD27, CD28, CD47, TIGIT, GITR, or OX40. Some of these genetically modified non-human animals are described, e.g., in PCT/CN2017/090320, PCT/CN2017/099577, PCT/CN2017/099575, PCT/CN2017/099576, PCT/CN2017/099574, PCT/CN2017/106024; each of which is incorporated herein by reference in its entirety.

In some embodiments, the CD132 knockout can be directly performed on a genetically modified animal having a human or chimeric PD-1, CTLA-4, LAG-3, BTLA, TIM-3, PD-L1, 4-1BB, CD27, CD28, CD47, TIGIT, GITR, or OX40 gene.

In some embodiments, the CD132 knockout can be directly performed on a B2m knockout mouse or a Foxn1 knockout mouse.

As these proteins may involve different mechanisms, a combination therapy that targets two or more of these proteins thereof may be a more effective treatment. In fact, many related clinical trials are in progress and have shown a good effect. The CD132 knockout animal model, and/or the CD132 knockout animal model with additional genetic modifications can be used for determining effectiveness of a combination therapy.

In some embodiments, the combination of agents can include one or more agents selected from the group consisting of paclitaxel, cisplatin, carboplatin, pemetrexed, 5-FU, gemcitabine, oxaliplatin, docetaxel, and capecitabine.

In some embodiments, the combination of agents can include one or more agents selected from the group consisting of campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and methotrexate.

In some embodiments, the combination of agents can include one or more antibodies that bind to CD47, PD-1, CTLA-4, LAG-3, BTLA, TIM-3, PD-L1, 4-1BB, CD27, CD28, CD47, TIGIT, GITR, and/or OX40.

Alternatively or in addition, the methods can also include performing surgery on the subject to remove at least a portion of the cancer, e.g., to remove a portion of or all of a tumor(s), from the subject.

EXAMPLES

The invention is further described in the following examples, which do not limit the scope of the invention described in the claims.

Materials and Methods

The following materials were used in the following examples.

NOD/scid mice were purchased from Beijing HFK Bioscience Co., Ltd.

BALB/c mice and BALB/c Nude mice were purchased from Beijing Vital River Laboratory Animal Technology Co., Ltd.

Ambion™ in vitro transcription kit was purchased from Ambion, Inc. The catalog number is AM1354.

Raji cells were purchased from the American Type Culture Collection (ATCC).

*E. coli* TOP10 competent cells were purchased from the Tiangen Biotech (Beijing) Co. The catalog number is CB104-02.

EcoRI, BamHI, and BbsI were purchased from NEB. The catalog numbers are R3101M, R3136M, and R0539L.

Kanamycin was purchased from Amresco. The catalog number is 0408.

pHSG299 plasmids were purchased from Takara. The catalog number is 3299.

KOD enzyme was purchased from Toyobo. The catalog number is KOD-101.

Cas9 mRNA was obtained from SIGMA. The catalog number is CAS9MRNA-1EA.

UCA kit was obtained from Beijing Biocytogen Co., Ltd. The catalog number is BCG-DX-001.

Mouse anti-human mitochondria antibody was purchased from Millipore. The catalog number is MAB1273; Anti-mouse CD3 antibody (PerCP) was obtained from Biolegend. The catalog number is 100326.

Anti-mouse CD4 antibody (FITC) was obtained from Biolegend. The catalog number is 116003.

Anti-mouse CD8 antibody (PE) was obtained from Biolegend. The catalog number is 100708.

Anti-mouse CD19 antibody (FITC) was obtained from Biolegend. The catalog number is 115506.

Anti-mouse CD49b antibody (APC) was obtained from Biolegend. The catalog number is 108909.

Gemcitabine (Gemcitabine HCl for injection; 1 g/vial) was from LILLY FRANCE.

Cisplatin (for injection; 50 ml:50 mg/vial) was from Hospira Australia Pty Ltd.

Capecitabine (Capecitabine tablets; 0.5 g*12 tablets per package) was from Shanghai Roche Pharmaceutical Co., Ltd.

Docetaxel (for injection; 0.5 ml: 20 mg/vial) was from Jiangsu Hengrui Pharmaceutical Co., Ltd.

Paclitaxel (for injection; 5 ml:30 mg/vial) was from Beijing SL PHARM.

Carboplatin was purchased from MCE (MedChemExpress). The catalog number is HY-17393.

Pemetrexed (for injection; 0.2 g/vial) was from Qilu Pharmaceutical Co., Ltd. 5-FU (fluorouracil; 0.25 g: 10 ml/vial, 5 vials per package) was from Tianjin Kingyork Pharmaceutical Co., Ltd.

Oxaliplatin (for injection; 50 mg/bottle) was from Jiangsu Hengrui Pharmaceutical Co., Ltd.

S-1 (Tegafur, Gimeracil and Oteracil Porassium Capsules; 20 mg*42 tablets per package) was from Shandong New Times Pharmaceutical Co., Ltd.

Example 1: sgRNAs for CD132

The target sequence determines the targeting specificity of small guide RNA (sgRNA) and the efficiency of Cas9 cleavage at the target site. Therefore, target sequence selection is important for sgRNA vector construction.

The mice used in the examples were NOD/scid mice.

Several sgRNAs were designed for the mouse CD132 gene. The target sequences for these sgRNAs are shown below:

```
sgRNA-1 target sequence (SEQ ID NO: 1):
5'-ccaccggaagctacgacaaaagg-3' sgRNA-2 target sequence (SEQ ID NO: 2):
5'-tctctacagcgtggtttctaagg-3' sgRNA-3 target sequence (SEQ ID NO: 3):
5'-ggcttgtgggagagtggttcagg-3' sgRNA-4 target sequence (SEQ ID NO: 4):
5'-ccacgctgtagagagagggggggg-3' sgRNA-5 target sequence (SEQ ID NO: 5):
5'-agggggaggttagcgtcacttagg-3' sgRNA-6 target sequence (SEQ ID NO: 6):
5'-gaaatcgaaacttagccccaagg-3' sgRNA-7 target sequence (SEQ ID NO: 7):
5'-gcagcctgcatagcccttactgg-3' sgRNA-8 target sequence (SEQ ID NO: 8):
5'-ccctactcaccttggcaatctgg-3'
``` sgRNA-1, sgRNA-2, sgRNA-3, and sgRNA-4 target the 5'-end target site and sgRNA-5, sgRNA-6, sgRNA-7, and sgRNA-8 target the 3'-end target site. Among them, the target sites for sgRNA-1, sgRNA-2, and sgRNA-4 are located upstream of exon 1 of the mouse endogenous CD132 gene (Gene ID: 16186). The target site for sgRNA-3 is located on exon 1 of CD132. The target sites for sgRNA-5, sgRNA-6, sgRNA-7, and sgRNA-8 are all located on exon 8 of the mouse endogenous CD132 gene.

Example 2. sgRNA Selection

The UCA kit was used to detect the activities of sgRNAs (FIG. 1). The results show that the sgRNAs had different activities. Two of them (sgRNA3 and sgRNA6) were selected for follow-up experiments. Single strand oligonucleotides were synthesized for sgRNA3 and sgRNA6.

TABLE 2

Oligonucleotide sequences for sgRNA3 and sgRNA6

| Oligonucleotide sequences for sgRNA3 | |
|---|---|
| SEQ ID NO: 9 | Forward:<br>5'-*caccggcttgtgggagagtggttc*-3' |
| SEQ ID NO: 10 | Reverse:<br>5'-*aaacgaaccactctcccacaagcc*-3' |
| Oligonucleotide sequences for sgRNA6 | |
| SEQ ID NO: 11 | Forward:<br>5'-*caccggaaatcgaaacttagcccca*-3' |
| SEQ ID NO: 12 | Reverse:<br>5'-*aaactggggctaagtttcgatttcc*-3' |

Figure 2:
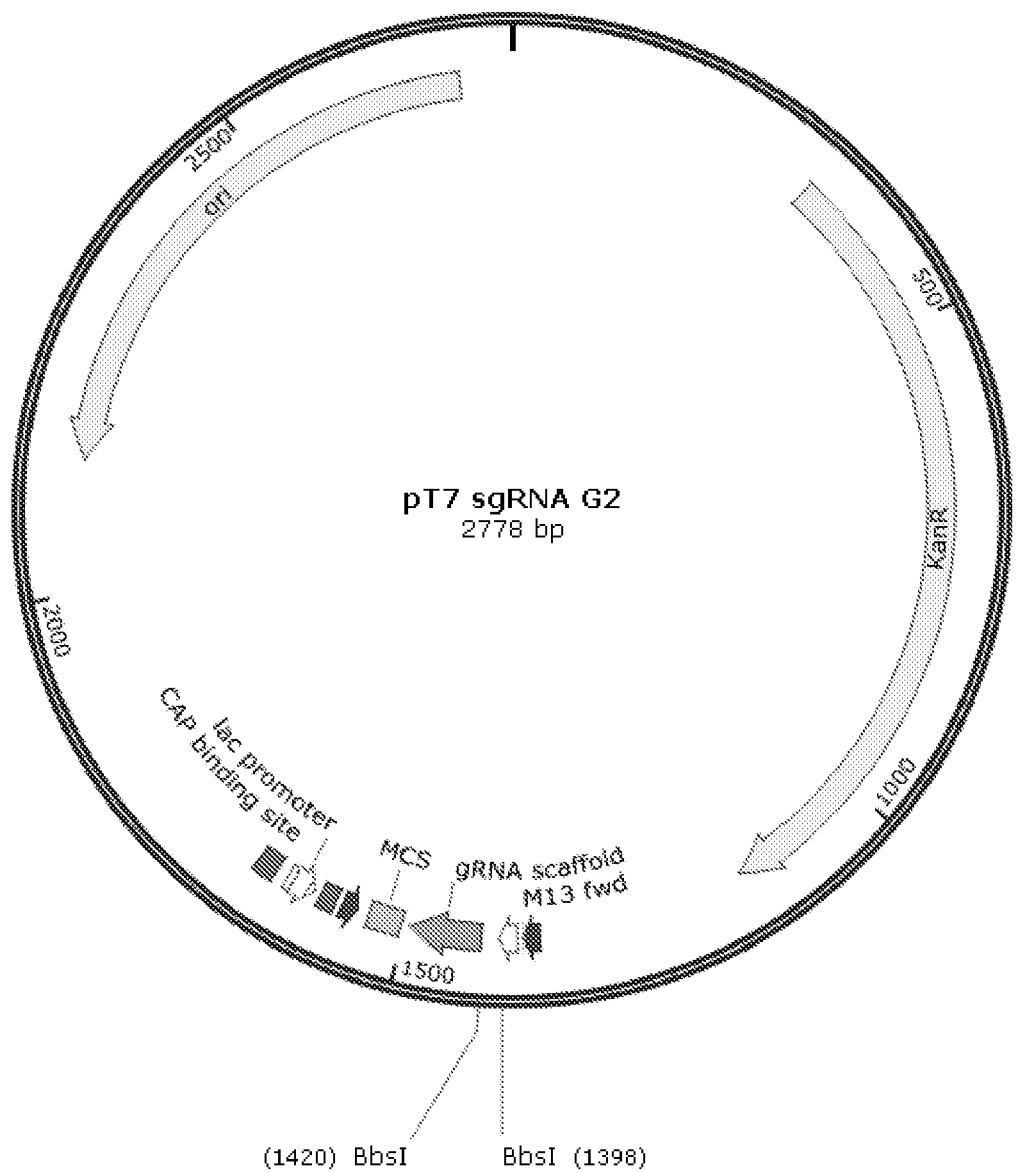
FIG. 2 is a schematic diagram showing pT7-sgRNA plasmid map.

Example 3. Construction of pT7-sgRNA G2 Vector pT7-sgRNA G2 vector map is shown in FIG. 2. The DNA fragment containing T7 promoter and sgRNA scaffold was synthesized, and linked to the backbone vector pHSG299 by restriction enzyme digestion (EcoRI and BamHI) and ligation. The plasmid sequences were confirmed by sequencing.

The DNA fragment containing the T7 promoter and sgRNA scaffold (SEQ ID NO: 13) is shown below:

GAATTCTAATACGACTCACTATAGGGGGTCTTCGAGAAGACCTGTTTT

AGAGCTAGAAATAGCAAGTTAAAATAAGGCTAGTCCGTTATCAACTTG

AAAAAGTGGCACCGAGTCGGTGCTTTTAAAGGATCC

Example 4. Construction of pT7-IL-3 and pT7-IL-6 Vectors

After annealing the oligonucleotides obtained in Example 2, the product was ligated into the pT7-sgRNA plasmid (the plasmid was first treated by BbsI).

TABLE 3

| The ligation reaction conditions (10 μL) | |
| --- | --- |
| Double stranded fragment | 1 μL (0.5 μM) |
| pT7-sgRNA vector | 1 μL (10 ng) |
| T4 DNA Ligase | 1 μL (5U) |
| 10× T4 DNA Ligase buffer | 1 μL |
| 50% PEG4000 | 1 μL |
| H$_2$O | Add to 10 μL |

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Clones were randomly selected and sequenced to verify their sequences. The pT7-IL-3 and pT7-IL-6 vectors with correct sequences were selected for subsequent experiments.

Example 5. Microinjection and Embryo Transfer

The pre-mixed Cas9 mRNA, in vitro transcription products of pT7-IL-3 and pT7-IL-6 plasmids were injected into the cytoplasm or nucleus of NOD/scid mouse fertilized eggs with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium to culture for a short time and then was transplanted into the oviduct of the recipient mouse to produce the genetically modified mice (F0 generation). The mice population was further expanded by cross-mating and self-mating to establish stable mouse lines. These genetically modified mouse model (CD132 knockout) was named as B-NDG mouse.

Example 6. Genotype Verification

PCR analysis was performed to determine whether CD132 has been successfully knocked out. The PCR reaction conditions are shown in the tables below.

TABLE 4

| The PCR reaction system (20 μL) | |
| --- | --- |
| 10× KOD buffer | 2 μL |
| dNTP (2 mM) | 2 μL |

TABLE 4-continued

| The PCR reaction system (20 μL) | |
| --- | --- |
| MgSO$_4$ (25 mM) | 0.8 μL |
| Upstream primer (10 μM) | 0.6 μL |
| Downstream primer (10 μM) | 0.6 μL |
| Mouse tail genomic DNA | 200 ng |
| KOD (200 U) | 0.6 μL |
| H$_2$O | Add to 20 μL |

TABLE 5

| The PCR reaction conditions | | |
| --- | --- | --- |
| Temperature | Time | Cycles |
| 95° C. | 5 min | 1 |
| 95° C. | 30 sec | 15 |
| 67° C. | 30 sec | |
| 72° C. | 1 kb/min | |
| 72° C. | 10 min | 1 |
| 4° C. | 10 min | 1 |

The primers are shown below:

```
Upstream primer
PCR-1 (SEQ ID NO: 14):
5'-AAGATAGCCTAGAGGGAAAAGGTGG-3';

Downstream primer
PCR-2 (SEQ ID NO: 15):
5'-AGGTAGAAAAAGGGAGGGAGAATCC-3'
```

If CD132 in the mouse has been successfully knocked out, the size of the PCR product should be about 609 bp; otherwise, there are no bands for PCR products.

Figure 3:
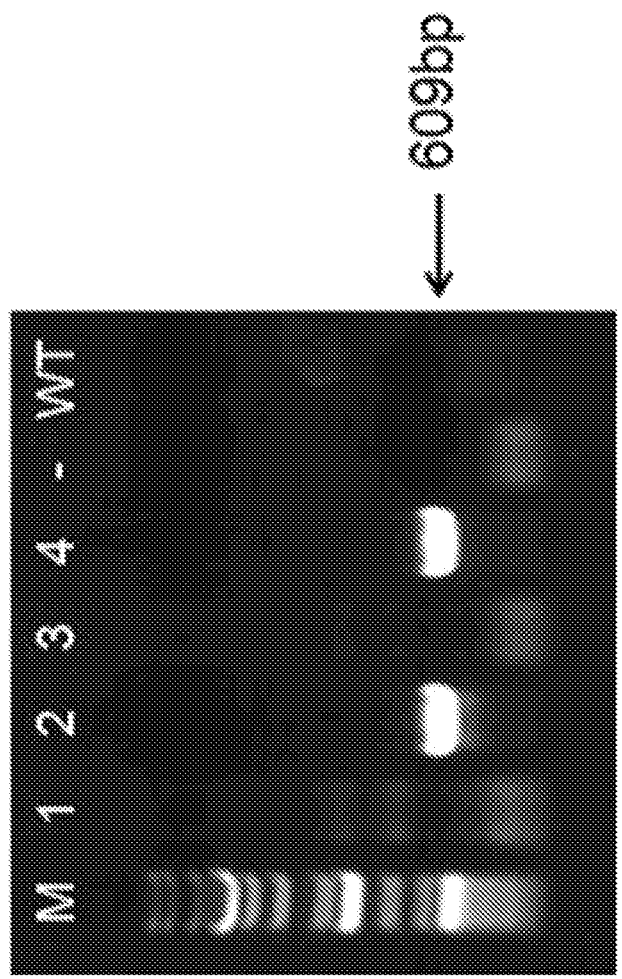
FIG. 3 shows PCR identification results for samples collected from mouse tails (M is the Marker; WT is wild-type; mice labeled with No. 2 and 4 are CD132 knockout mice).

As shown in FIG. 3, the PCR results showed that mice labeled with No. 2 and 4 were positive.

Example 7. Characteristics of B-NDG Mice

Three B-NDG mice were selected for experiments, and three BALB/c mice and three NOD/scid mice were also included in the experiments.

The spleens of these mice were collected after euthanasia, and the spleen samples were grinded. The ground samples were then passed through 70 m cell mesh. The filtered cell suspensions were centrifuged and the supernatants were discarded. Erythrocyte lysis solution was added to the sample, which was lysed for 5 minutes and neutralized by PBS solution. The solution was centrifuged again and the supernatants were discarded. The cells were washed with PBS for one more time before FACS analysis.

The cells were labeled by appropriate antibodies described herein. The percentages of CD3+ T cells, CD3− CD19+ B cells, and CD3− CD49b+NK cells among all leukocytes (CD45+ cells) were analyzed (Table 6). The T cells (CD3+ cells) were further analyzed. The percentages of CD3+ CD4+ T cells and CD3+ CD8+ T cells among all T cells were also calculated.

Table 6 and Table 7 shows the percentage of CD3+ T cells, CD3−CD19+ B cells, and CD3− CD49b+NK cells in leukocytes, and the percentage of CD3+ CD4+ T cells and CD3+ CD8+ T cells in T cells.

TABLE 6

Cell surface marker expressions

| Cell surface markers | | Balb/c (n = 3) | NOD/scid (n = 3) | B-NDG (n = 3) |
|---|---|---|---|---|
| T cells | CD3+ | 32.48% | 0.75% | 0.56% |
| CD4+ T cells | CD3+ CD4+ | 82.01% | 1.64% | 0.07% |
| CD8+ T cells | CD3+ CD8+ | 6.15% | 0.23% | 0.05% |
| B cells | CD3− CD19+ | 57.35% | 0.17% | 0.03% |
| NK cells | CD3− CD49b+ | 2.82% | 13.33% | 1.37% |

Figure 4:
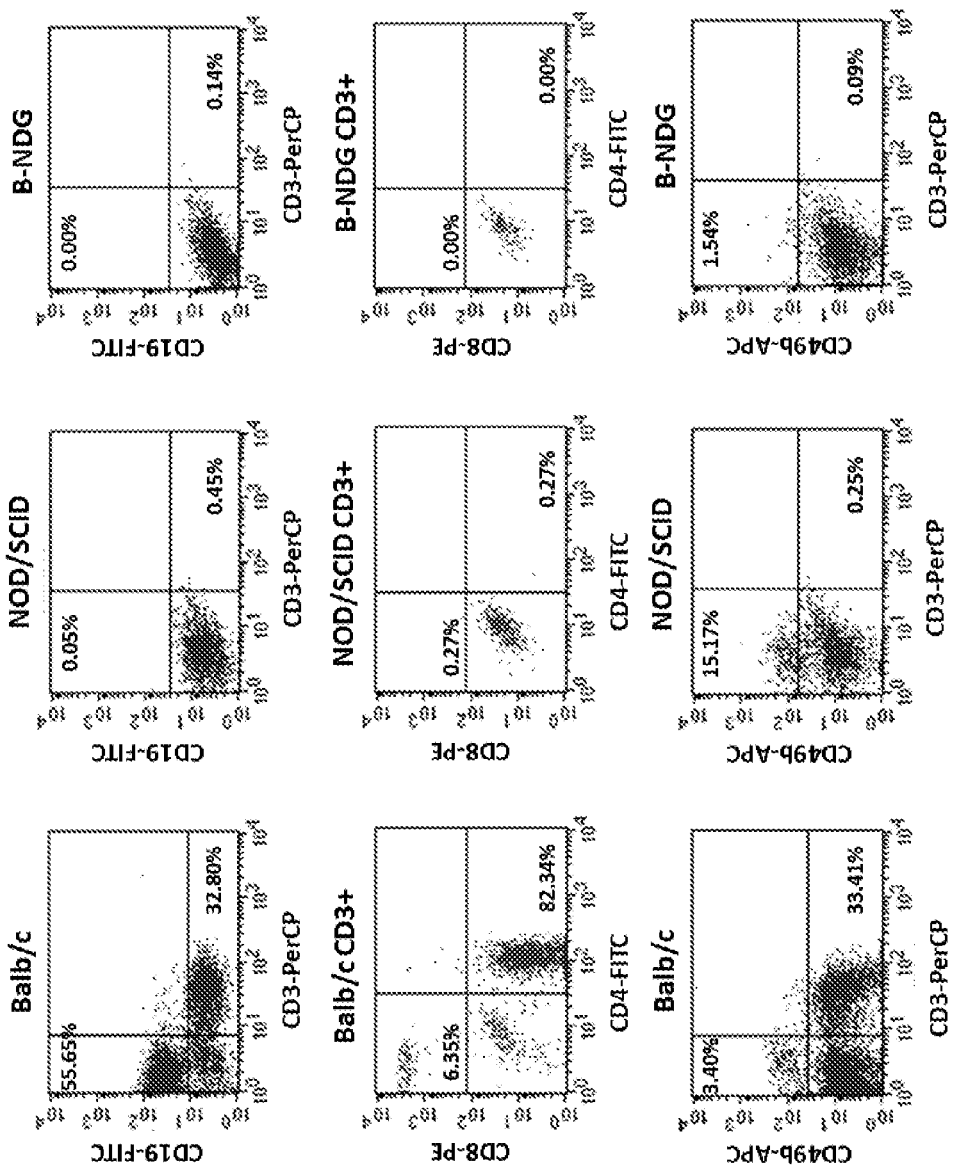
FIG. 4 shows flow cytometry results for the spleen cells of a BALB/c mouse, a NOD/scid mouse, and a B-NDG mouse. The results show that the B-NDG mouse almost completely lacked T cells, B cells, or NK cells.

Table 6 compares the percentages in B-NDG mice, BALB/c mice and NOD/scid mice. The flow cytometry results are shown in FIG. 4. The flow cytometry results showed that B-NDG immune-deficient mice lacked T cells, B cells, and NK cells as compared to wild-type BALB/c mice. As compared to NOD/scid mice, the percentage of T cells, B cells, and NK cells in B-NDG were even smaller. The results showed that by completely knocking out the CD132 gene in NOD/scid background mice, the degree of immunodeficiency in the mice can be further increased. The B-NDG immune-deficient mice prepared by this method as described herein almost completely lack T cells, B cells, and NK cells.

TABLE 7

Flow cytometry results for T cells, B cells, and NK cells in B-NDG mice

| Cell surface markers | | B-NDG #1 | B-NDG #2 | B-NDG #3 | Average | SD |
|---|---|---|---|---|---|---|
| T cells | CD3+ | 1.20% | 0.35% | 0.14% | 0.56% | 0.56% |
| CD4+ T cells | CD3+ CD4+ | 0.21% | 0.00% | 0.00% | 0.07% | 0.12% |
| CD8+ T cells | CD3+ CD8+ | 0.00% | 0.14% | 0.00% | 0.05% | 0.08% |
| B cells | CD3− CD19+ | 0.09% | 0.00% | 0.00% | 0.03% | 0.05% |
| NK cells | CD3− CD49b+ | 1.34% | 1.24% | 1.54% | 1.37% | 0.15% |

Table 7 lists flow cytometry results for T, B, and NK cells in three B-NDG mice. The results showed that in B-NDG mice, the percentage of T, B, NK cells in vivo was significantly smaller than that in NOD/scid background mice, and the variations among individual B-NDG mice were very small, demonstrating high consistency among B-NDG mice. The cells that express CD3+ CD4+, CD3+ CD8+, CD3− CD19+ surface markers were less than 0.5% of all leukocytes. The cells that express CD3+, CD3− CD49b+ surface markers were less than 2% of all leukocytes.

Example 8. Construction of Human Immune System in Immunodeficient Mice

In immunodeficient mice obtained by the methods as described herein, a human immune system was constructed by engraftment with human peripheral blood cells (hPBMC).

Figure 5:
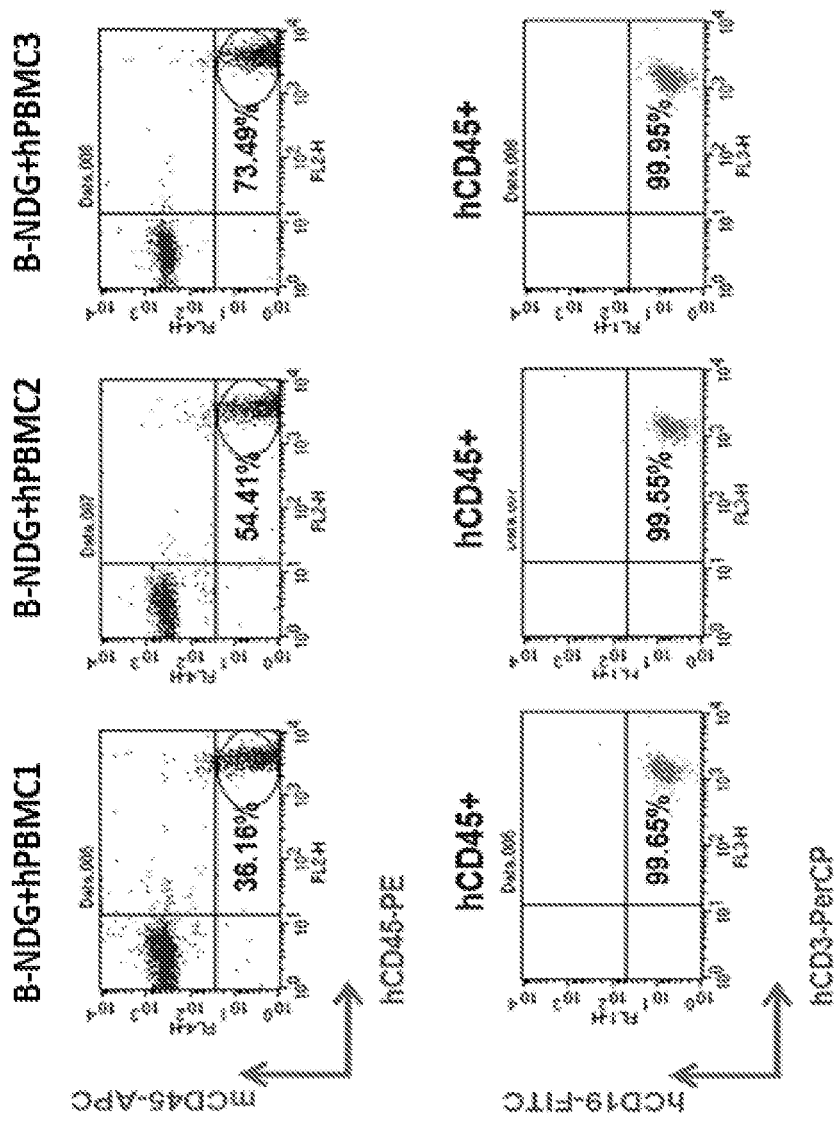
FIG. 5 shows flow cytometry results after human peripheral blood cells (hPBMCs) were injected into three B-NDG mice.

Three B-NDG immunodeficient mice were selected and $5 \times 10^6$ human peripheral blood cells (hPBMCs) were injected into the tail vein of each mouse. Blood was taken 24 days later for flow cytometry analysis. As shown in FIG. 5, the flow cytometry results showed that cells expressing human leukocyte surface molecular markers (human CD45) were detected in all three mice.

The results show that human peripheral blood cells engraftment on these B-NDG mice can create a humanized mouse model with the human immune system. Further analysis showed that human leukocytes (human CD45+ cells) were dominated by human T cells (human CD3+ cells).

Example 9. Comparative Analysis of Immunodeficient Mice

This Example compared the B-NDG immunodeficient mouse obtained by the methods described herein with some other immunodeficient mice.

Figure 6A:
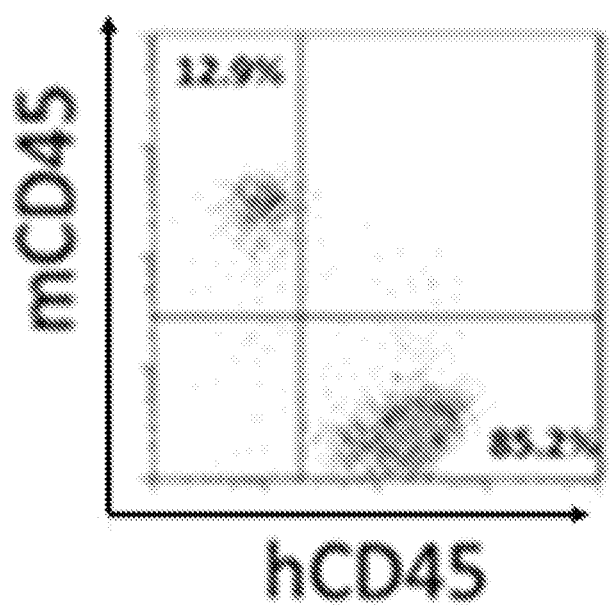
FIG. 6A shows flow cytometry results 10 weeks after human hematopoietic stem cells were injected into a B-NDG mouse.
Figure 6B:
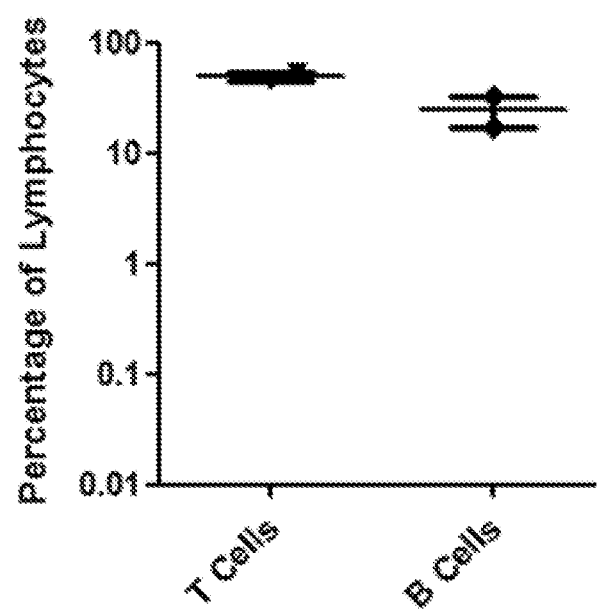
FIG. 6B shows the percentage of human T cells and human B cells in leukocytes 10 weeks after human hematopoietic stem cells were injected into a B-NDG mouse.

Human hematopoietic stem cells (CD34+) were used to reconstruct the immune system in immunodeficient mice. After irradiation of the recipient immunodeficient mice, human hematopoietic stem cells (CD34+) were injected into the mice to reconstruct the immune system. The proportions of human leukocytes (hCD45+), human T cells (hCD3+) and human B cells (hCD19+) in leukocytes were analyzed. The results of B-NDG mice are shown in FIGS. 6A-6B. The data for other immunodeficient mice are shown in Table 8 (data source: NSG mice: Ishikawa, Fumihiko, et al. "Development of functional human blood and immune systems in NOD/SCID/IL2 receptor γ chainnull mice." Blood 106.5 (2005): 1565-1573; NOG mice: Katano, Ikumi, et al. "NOD-Rag2null IL-2Rynull mice: an alternative to NOG mice for generation of humanized mice." Experimental animals 63.3 (2014): 321-330).

TABLE 8

Comparison of immunodeficient mice

| | B-NDG | NSG | NOG |
|---|---|---|---|
| hCD45+ (%) | 85.2% | 68.9% | 58% |
| hCD3+T (%) | 49% | 42.8% | 39% |
| hCD19+ B (%) | 25.2% | 7.8% | 16% |

The results show that B-NDG mice have the highest proportion of human-derived cells as compared to other immunodeficient mice. The proportions of differentiated human T cells and human B cells are also higher than the proportions in NSG and NOG mice, indicating that animals as prepared by the methods described herein are better animal models for human-derived cell transplantation and human immune system construction.

Example 10. Tumor Inoculation in Immunodeficient Mice

Experiments were performed to inoculate tumor cells in immunodeficient mice.

Figures 7A, 7B, 7C:
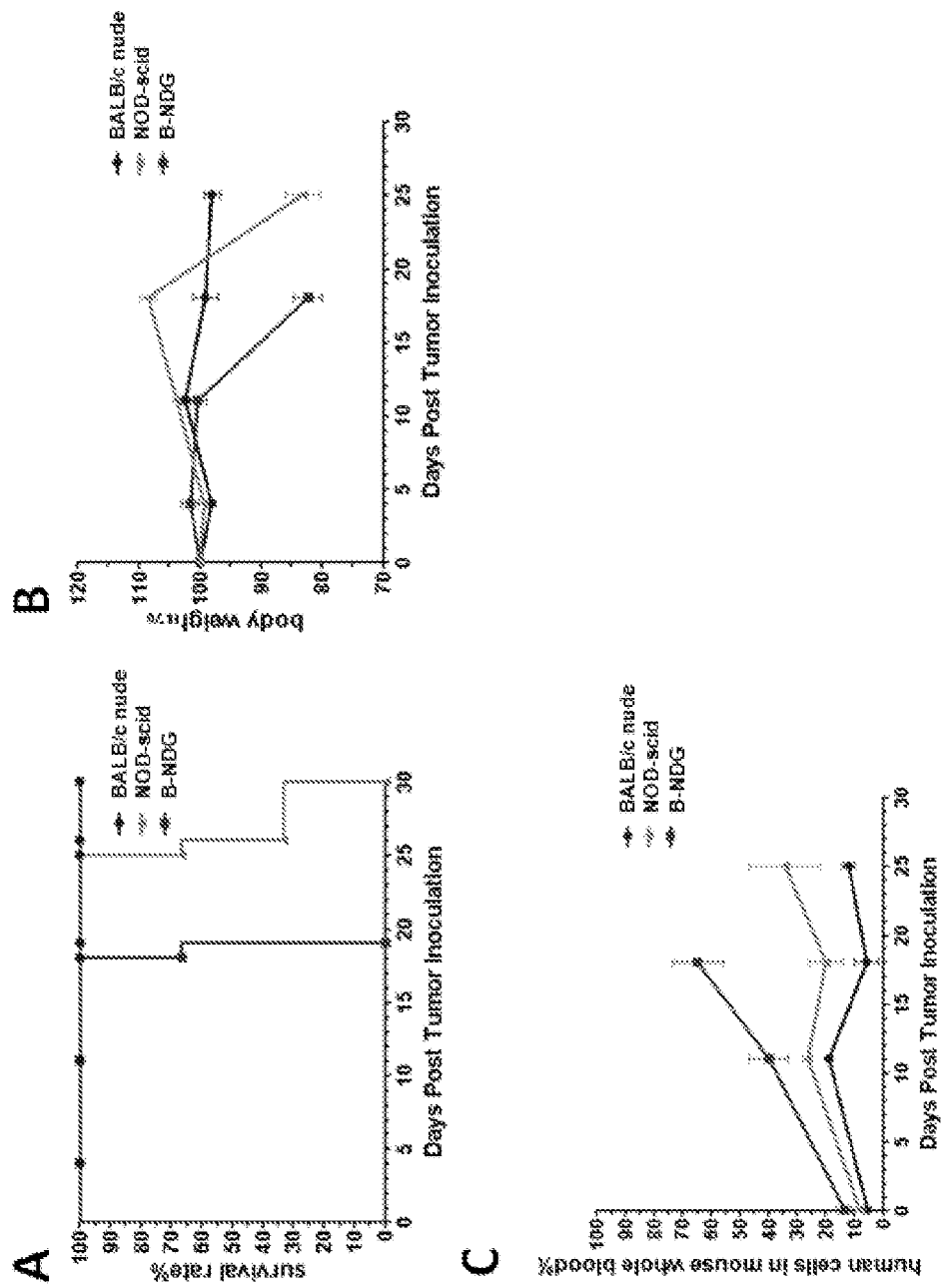
FIG. 7A shows the Kaplan-Meier survival curve of B-NDG, NOD/scid, BALB/c nude mice, wherein $5 \times 10^5$ of Raji cells were injected into each mouse.
FIG. 7B shows the percentage of weight change of B-NDG, NOD/scid, BALB/c nude mice, wherein $5\times10^5$ of Raji cells were injected into each mouse.
FIG. 7C shows the percentage of human cells in peripheral blood. Human cells were identified by performing q-PCR on 100 ul of whole blood collected from each mouse.

One BALB/c nude mouse, one NOD/scid mouse, and one B-NDG immunodeficient mouse were selected for experiments. $5 \times 10^5$ Raji cells were injected into the tail vein of each mouse. The survival status was shown in FIG. 7A. The percentages of body weight changes of the mice were shown in FIG. 7B. Euthanasia was performed when the body weight fell by more than 30%. The percentage change of human-derived cells in the peripheral blood was shown in FIG. 7C.

Figure 8:
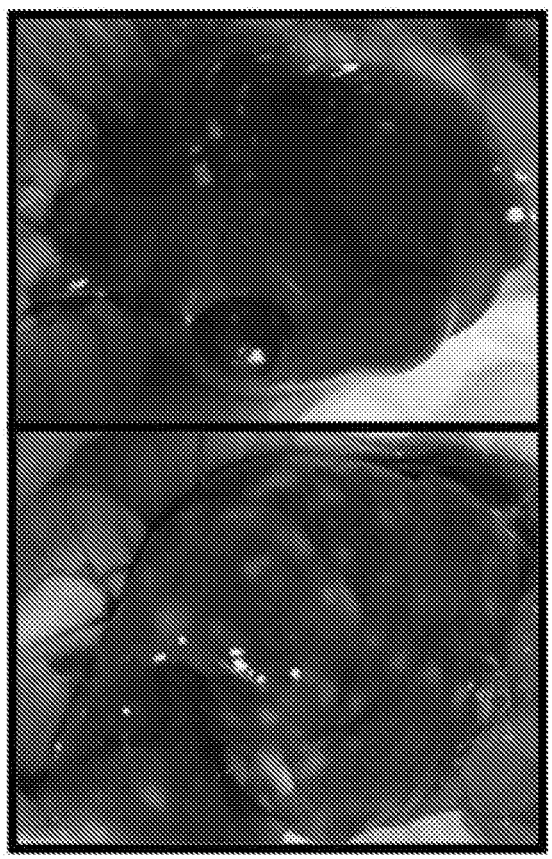
FIG. 8 is a set of images showing the liver of B-NDG and NOD/scid mouse, wherein $5\times10^5$ of Raji cells were injected into the mouse. Euthanasia was performed when the body weight fell by more than 30%.
Figure 9:
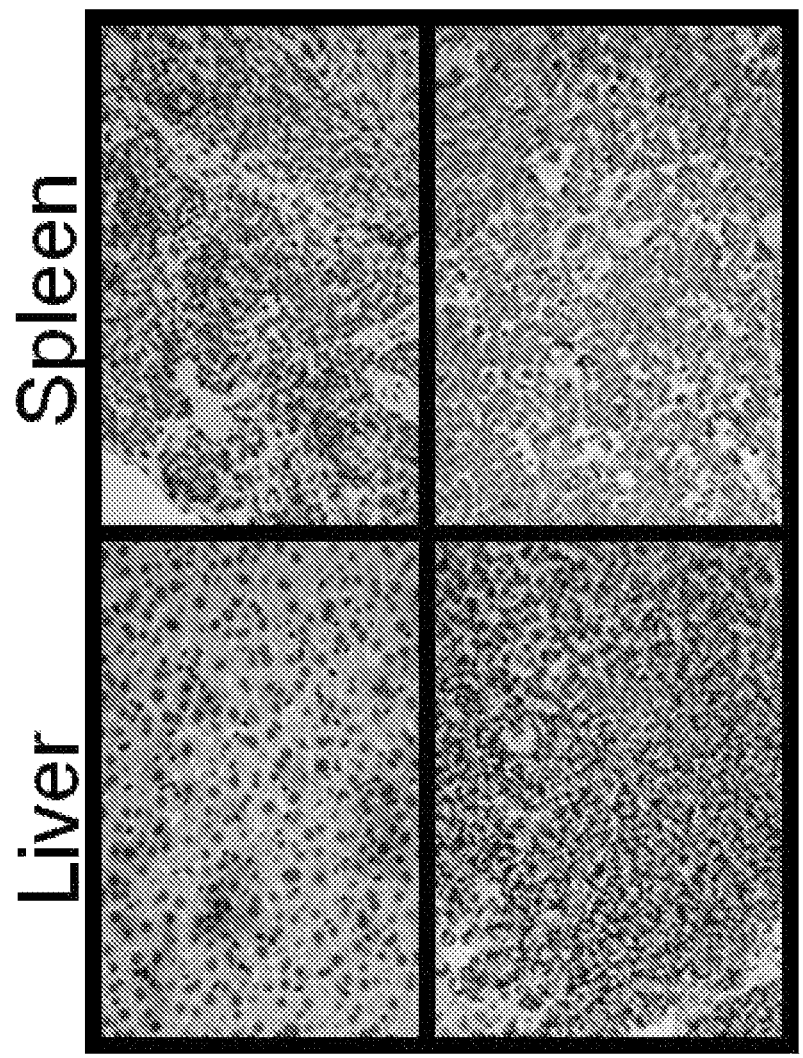
FIG. 9 is a set of immunochemistry images (400×) showing the liver and the spleen of B-NDG and NOD/scid mouse, wherein $5\times10^5$ of Raji cells were injected into each mouse. The cells were labeled by anti-human mitochondria antibodies.

The results showed that the growth rate of Raji cells in B-NDG immunodeficient mice was higher than the growth rates in other mice. The body weight decreased by more than 30% in B-NDG mice in about 18 days. After the mice were euthanized, it was determined that the whole liver of the B-NDG mice was covered by white tumor cells (FIG. 8). There were fewer tumor cells on the liver of NOD/scid mice at day 25. Immunohistochemistry was performed on the liver and spleen of these mice by using the mouse anti-human mitochondria antibody. As shown in FIG. 9, the staining signals for human mitochondria in the liver and the spleen of B-NDG mice were stronger than NOD/scid mice.

This example shows that Raji cells grow more quickly and formed tumors more easily in B-NDG mice than other immunodeficient mice.

Example 11. Drug Efficacy Testing in Immunodeficiency Mice

Human CD34+ hematopoietic stem cells can be injected to the B-NDG immunodeficient mice to build a human immune system and be used to test the efficacy of anti-tumor drugs (e.g., antibodies).

Figure 10A:
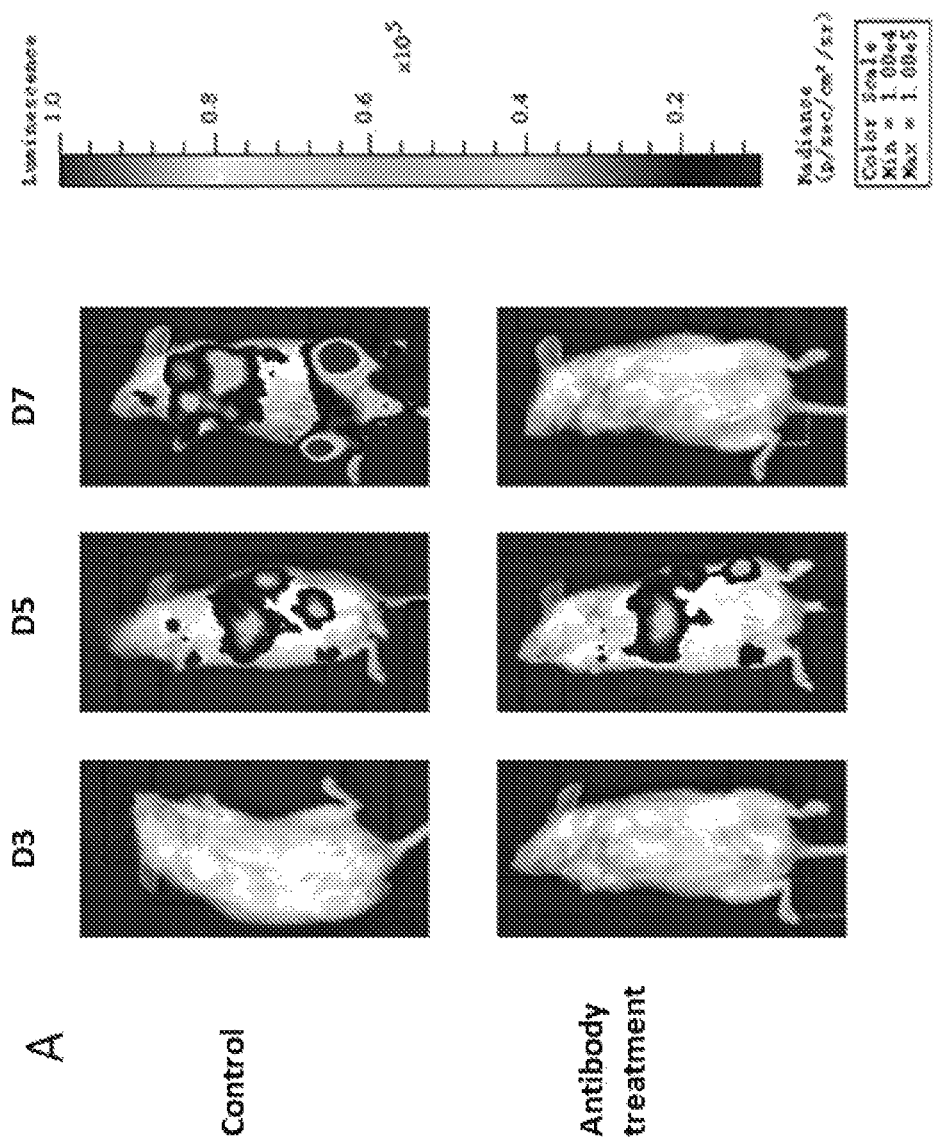
FIG. 10A is a set of images showing the tumor growth status at day 3, day 5, day 7 in B-NDG mice, wherein CD34+ cells were injected to the mice first, and then Raji cells were injected to the mice. The antibody treatment group was treated by an anti-human PD-1 antibody.
Figure 10B:
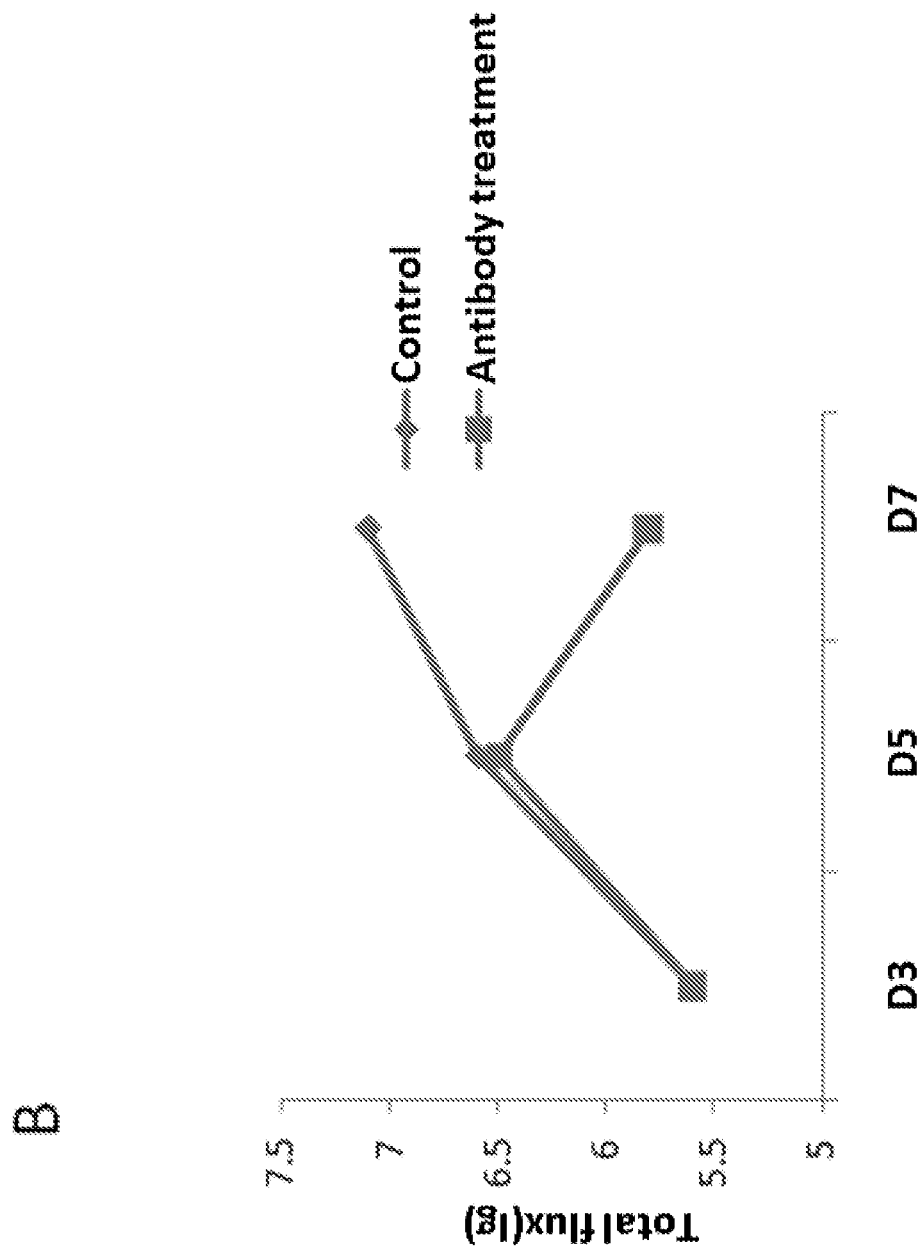
FIG. 10B is a graph showing total flux for tumor cells in the control group and the antibody treatment group.

Human CD34+ hematopoietic stem cells were injected into four B-NDG immunodeficient mice. After the human immune system was developed, $5\times10^5$ human B-cell lymphoma cells that were labeled by a luciferase gene were injected into these mice through the tail vein. After the tumor formed in vivo, anti-human PD-1 antibodies were injected to two randomly selected mice. The size of the tumor in mice was measured by in vivo imaging. The test results are shown in FIG. 10A and FIG. 10B. The results show that the tumor cells in the mice were significantly reduced 2 days after the injection of human anti-PD-1 antibody, whereas the tumors in the mice that were not treated by the human anti-PD-1 antibodies continued to grow and became metastatic.

As the PD-1 gene is mainly expressed on T cells, and immunodeficient mice do not have T cells in vivo, the T cells in these immunodeficient mice must be derived from human CD34+ cells. Example 9 shows that human CD34+ hematopoietic stem cells can be injected into B-NDG mice to reconstruct the immune system and produce human T lymphocytes. In the present example, after the injection of the anti-human PD-1 antibody, the PD-1 antigen on the surface of the T cells in the B-NDG mouse was blocked and inhibited, and the immune response was activated. As the result, the growth of the transplanted tumor cells was inhibited. The experiments show that the B-NDG mice prepared by the methods described herein can be used to reconstruct the immune system, screen new drugs, and test drug efficacy.

Example 12. Drug Efficacy Testing for Human Antibodies

Experiments were performed to test drug efficacy in the B-NDG immunodeficient mice.

Figure 11:
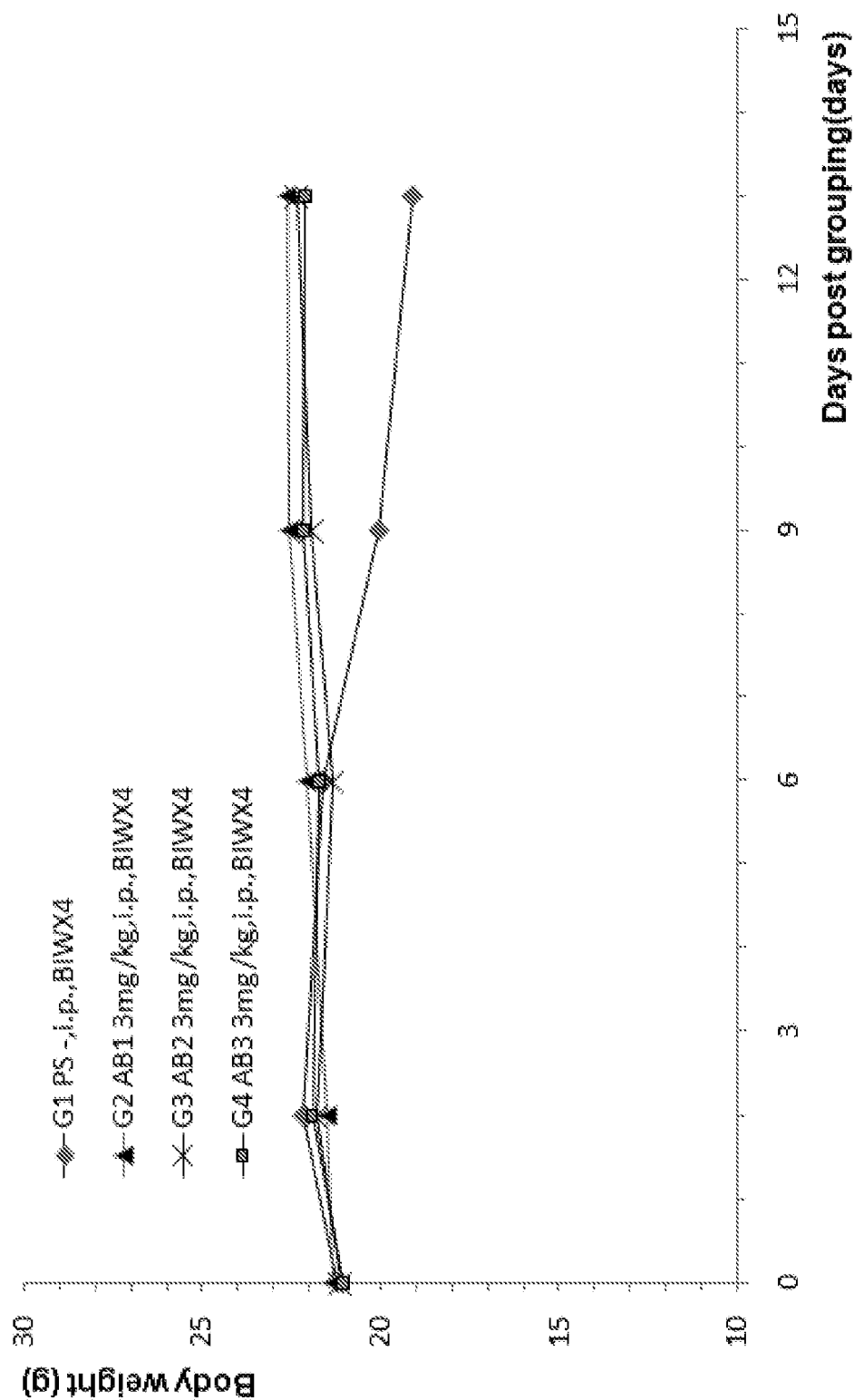
FIG. 11 is a graph showing the body weight of B-NDG mice after human B-cell lymphoma cells were injected into the B-NDG mice, and the mice were treated by three different anti-human CD47 antibodies (Ab-A, Ab-B, Ab-C).
Figure 12:
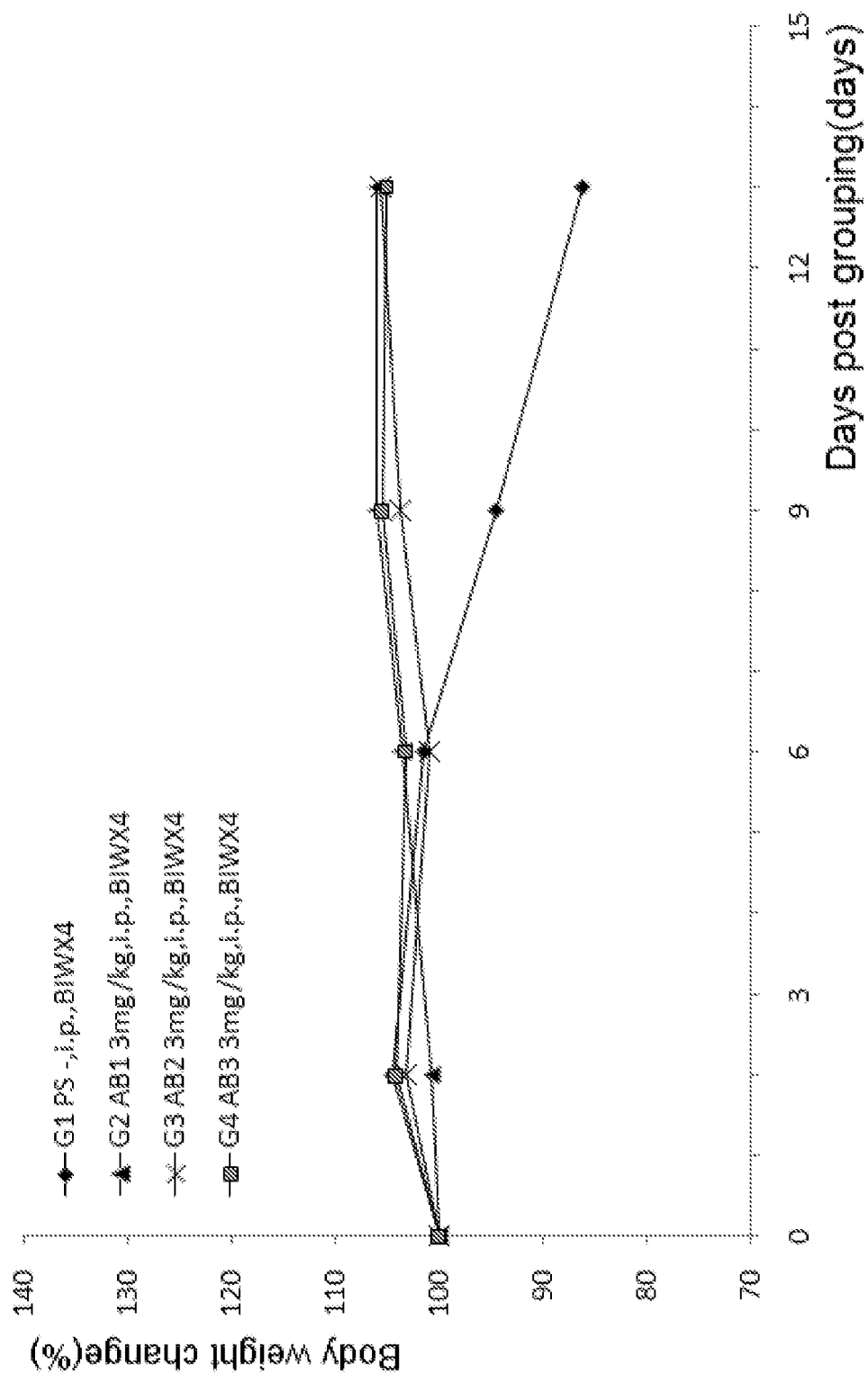
FIG. 12 is a graph showing the percentage of body weight change of B-NDG mice after human B-cell lymphoma cells were injected into the B-NDG mice, and the mice were treated by three different anti-human CD47 antibodies (Ab-A, Ab-B, Ab-C).

$1\times10^6$ human B-cell lymphoma cells that were labeled by a luciferase gene were injected into the tail vein of B-NDG mice (4-6 weeks). When the tumor formed in the mice, the mice were randomly divided to a control group and three treatment groups (n=5/group). The treatment groups were randomly selected for treatment with anti-human CD47 antibodies (Ab-A, Ab-B, Ab-C) at 3 mg/kg; the control group was injected with an equal volume of blank solvent. The antibodies and the blank solvent were administered through intraperitoneal injection twice a week (4 administrations in total). The tumor sizes were measured twice a week by the in vivo imaging system (6 times in total). Euthanasia was performed when the body weight decreased more than 20%. The body weight, body weight change percentage, and the signals for tumor cells were shown in FIGS. 11-13.

Figure 13:
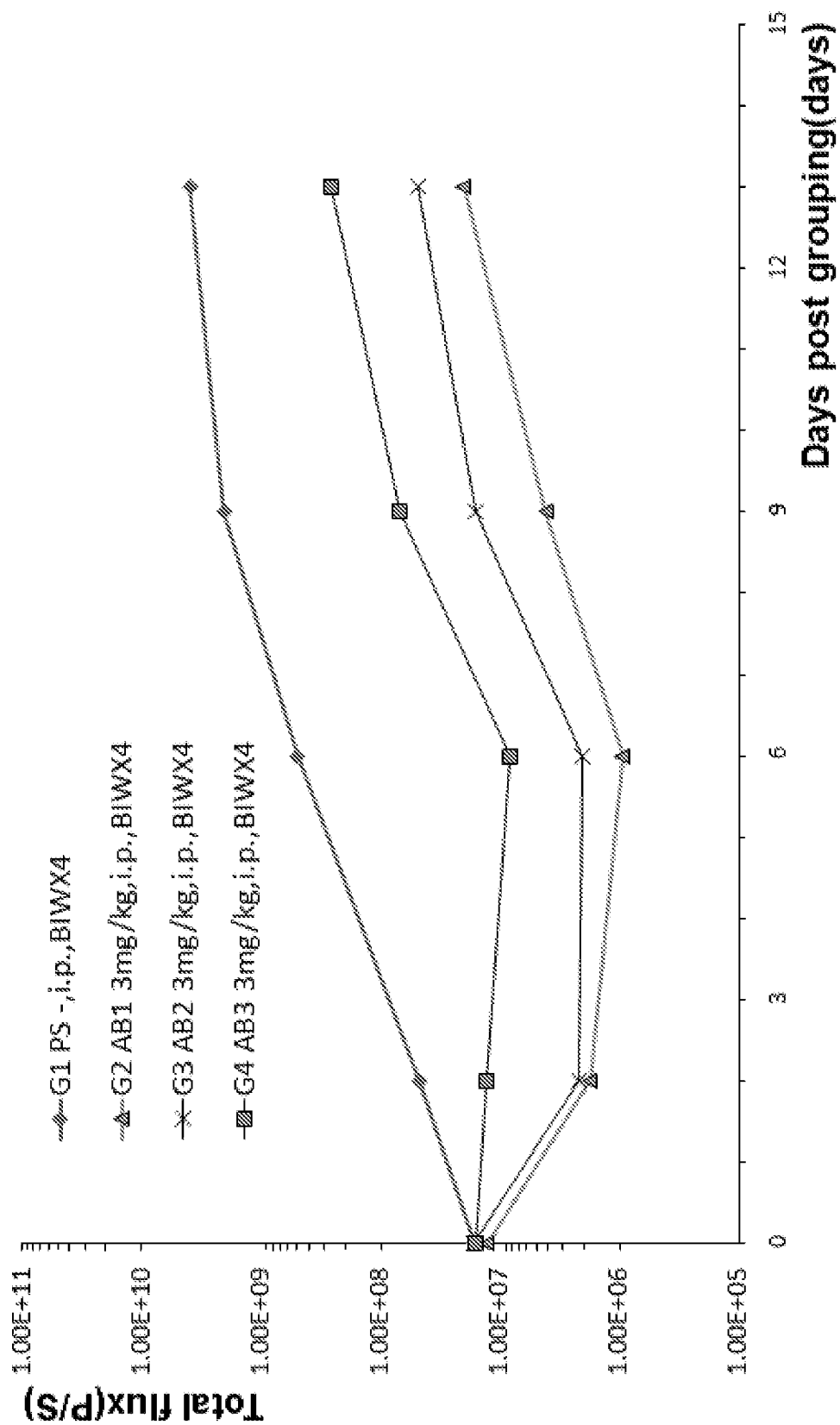
FIG. 13 is a graph showing total flux in B-NDG mice after human B-cell lymphoma cells were injected into the B-NDG mice, and the mice were treated by three different anti-human CD47 antibodies (Ab-A, Ab-B, Ab-C).
Figure 14:
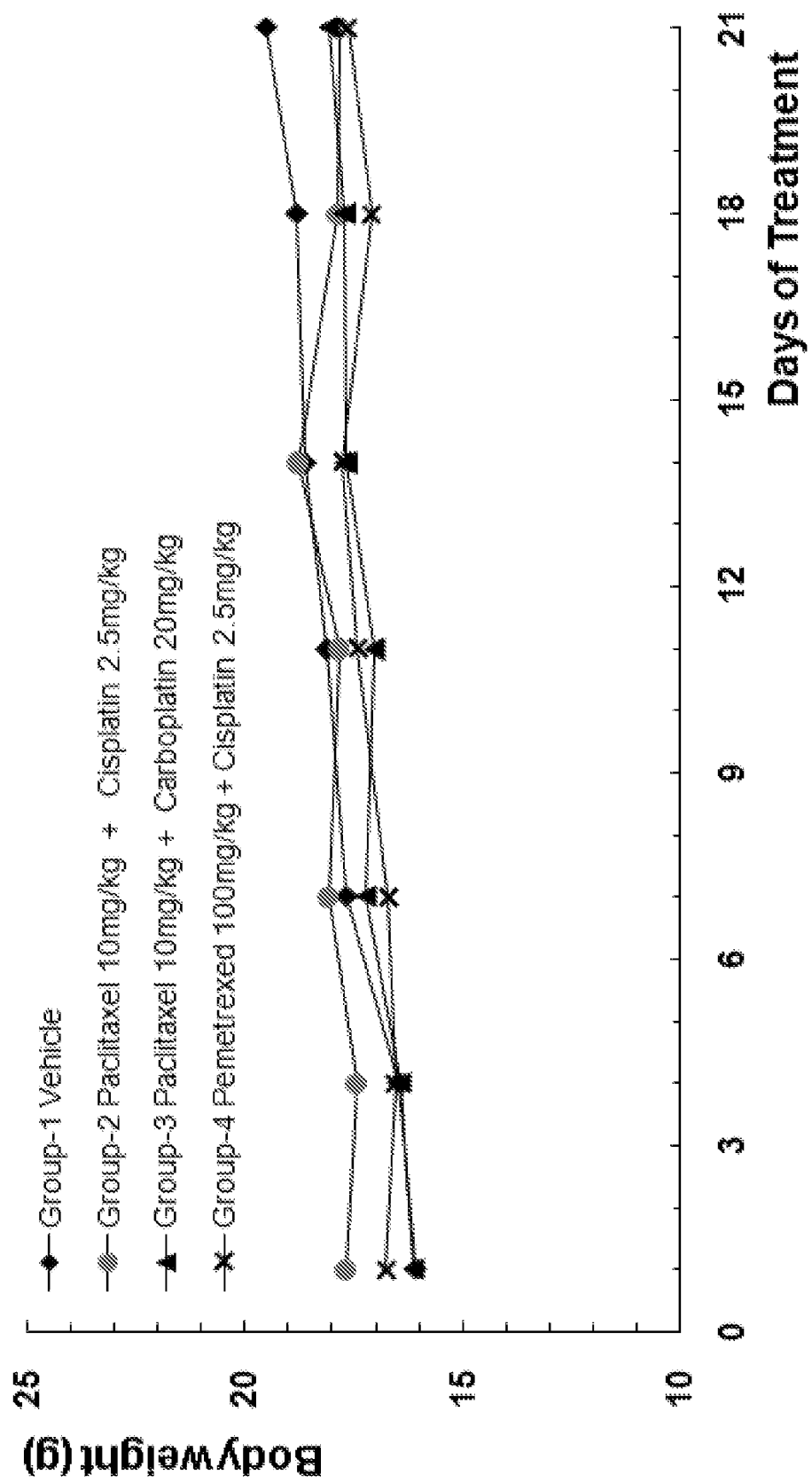
FIG. 14 is a graph showing the body weight of B-NDG mice after human primary lung carcinoma cells were injected into the B-NDG mice, and the mice were treated by the combination of (1) paclitaxel (10 mg/kg) and cisplatin (2.5 mg/kg), (2) paclitaxel (10 mg/kg) and carboplatin (20 mg/kg), or (3) pemetrexed (100 mg/kg) and cisplatin (2.5 mg/kg).
Figure 15:
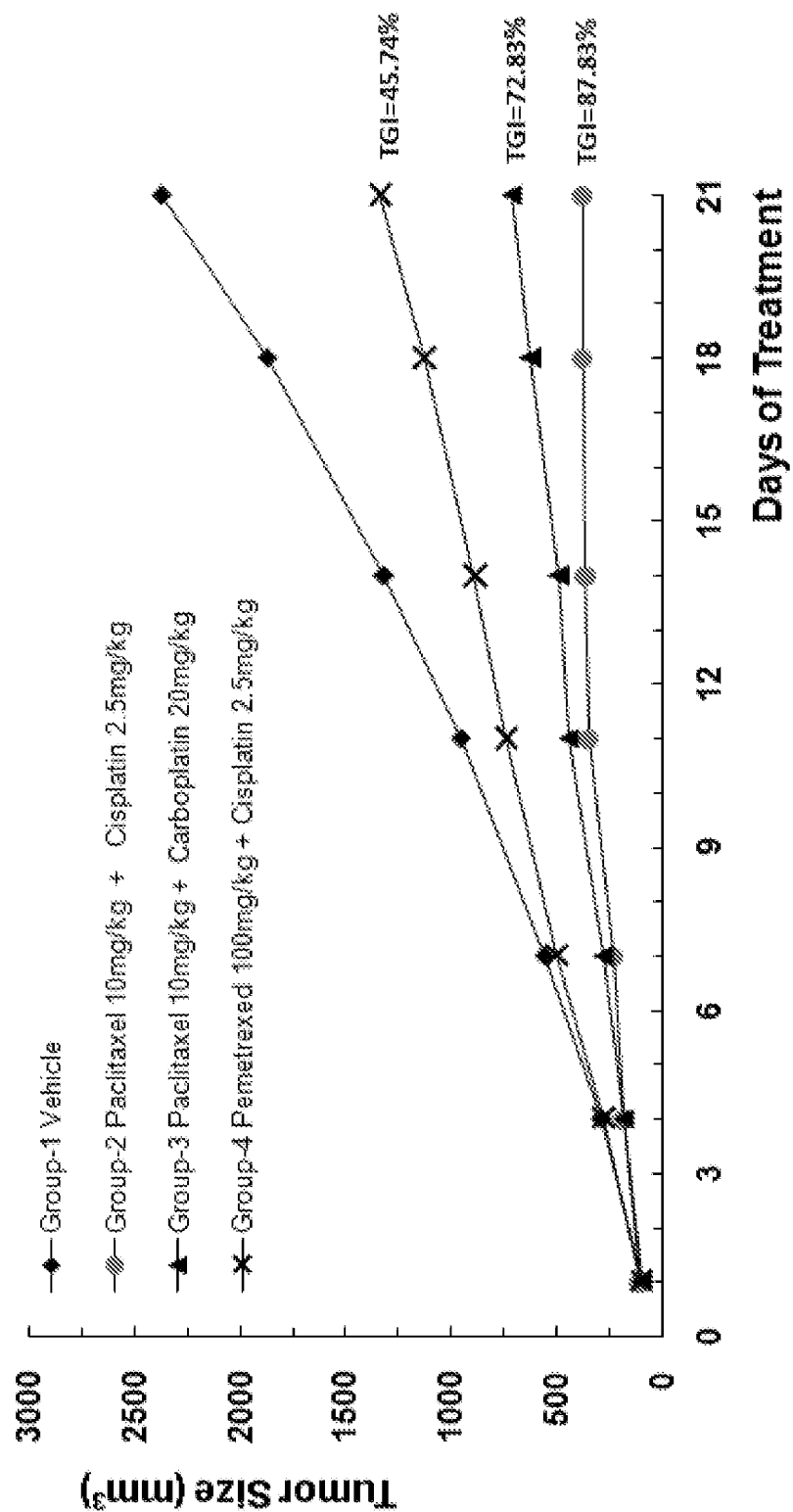
FIG. 15 is a graph showing tumor size in B-NDG mice after human primary lung carcinoma cells were injected into the B-NDG mice, and the mice were treated by the combination of (1) paclitaxel (10 mg/kg) and cisplatin (2.5 mg/kg), (2) paclitaxel (10 mg/kg) and carboplatin (20 mg/kg), or (3) pemetrexed (100 mg/kg) and cisplatin (2.5 mg/kg).
Figure 16:
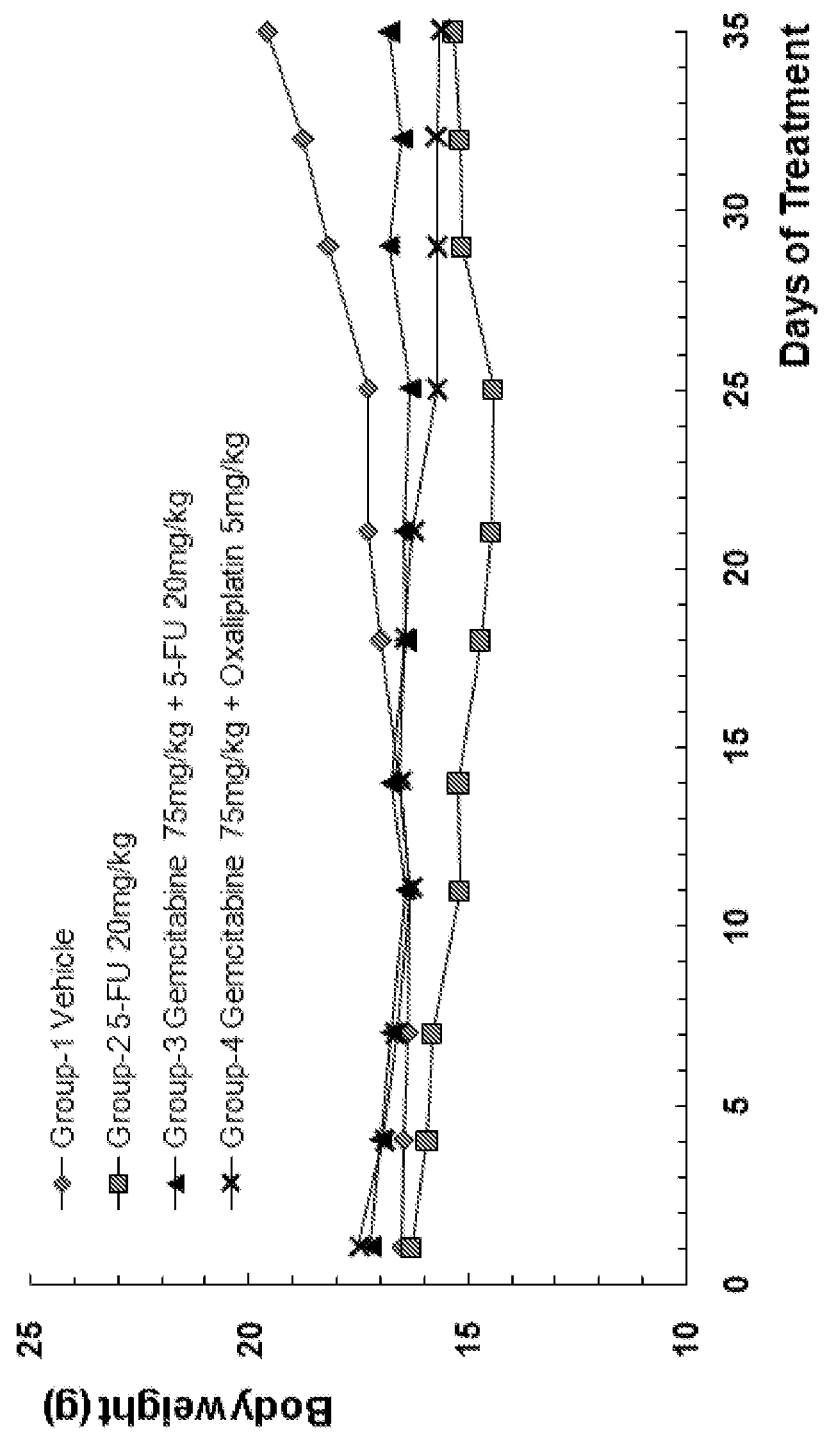
FIG. 16 is a graph showing the body weight of B-NDG mice after human primary lung carcinoma cells were injected into the B-NDG mice, and the mice were treated by (1) 5-FU (20 mg/kg), (2) gemcitabine (75 mg/kg) and 5-FU (20 mg/kg), or (3) gemcitabine (75 mg/kg) and oxaliplatin (5 mg/kg)
Figure 17:
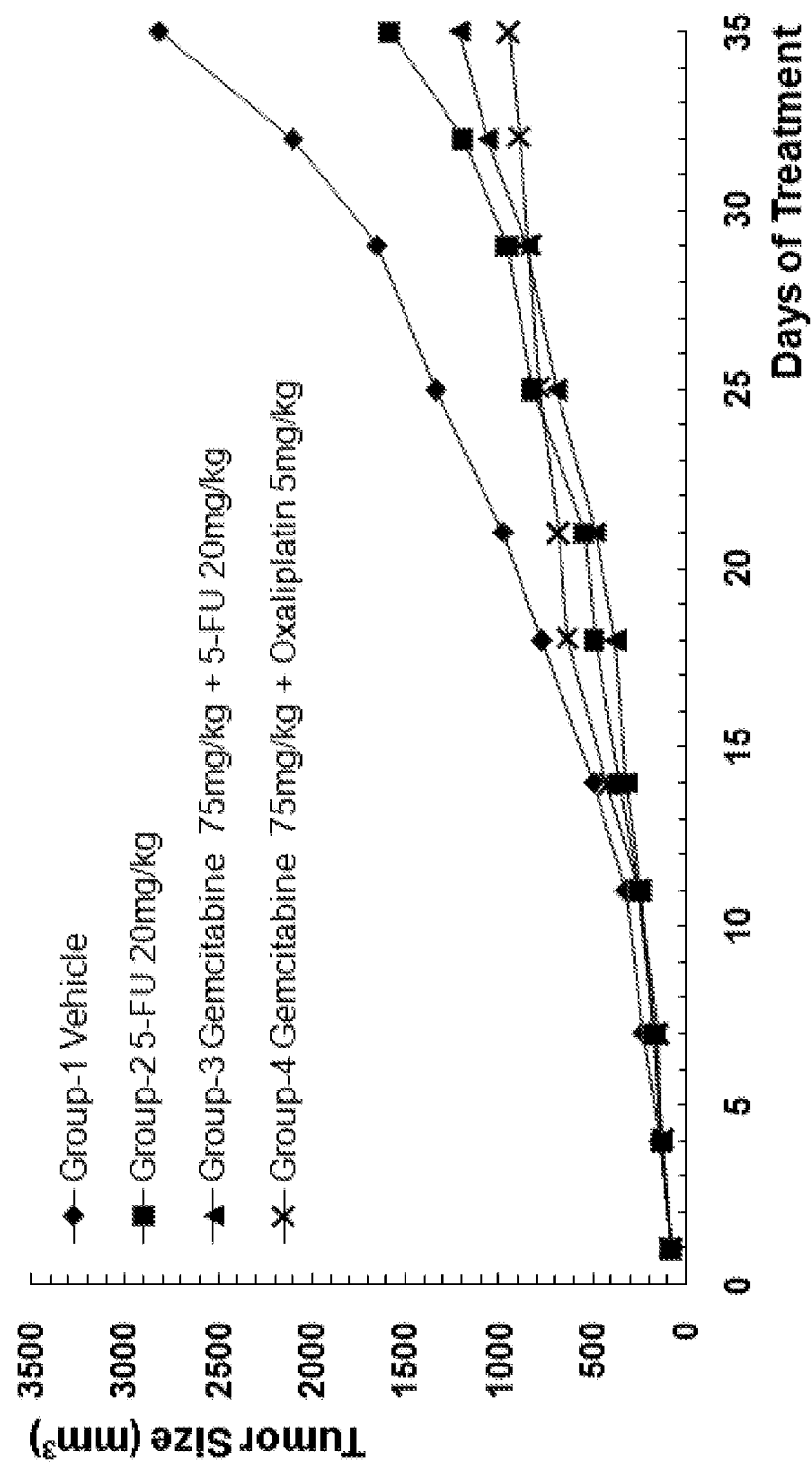
FIG. 17 is a graph showing the tumor size in B-NDG mice after human primary lung carcinoma cells were injected into the B-NDG mice, and the mice were treated by (1) 5-FU (20 mg/kg), (2) gemcitabine (75 mg/kg) and 5-FU (20 mg/kg), or (3) gemcitabine (75 mg/kg) and oxaliplatin (5 mg/kg).
Figure 18:
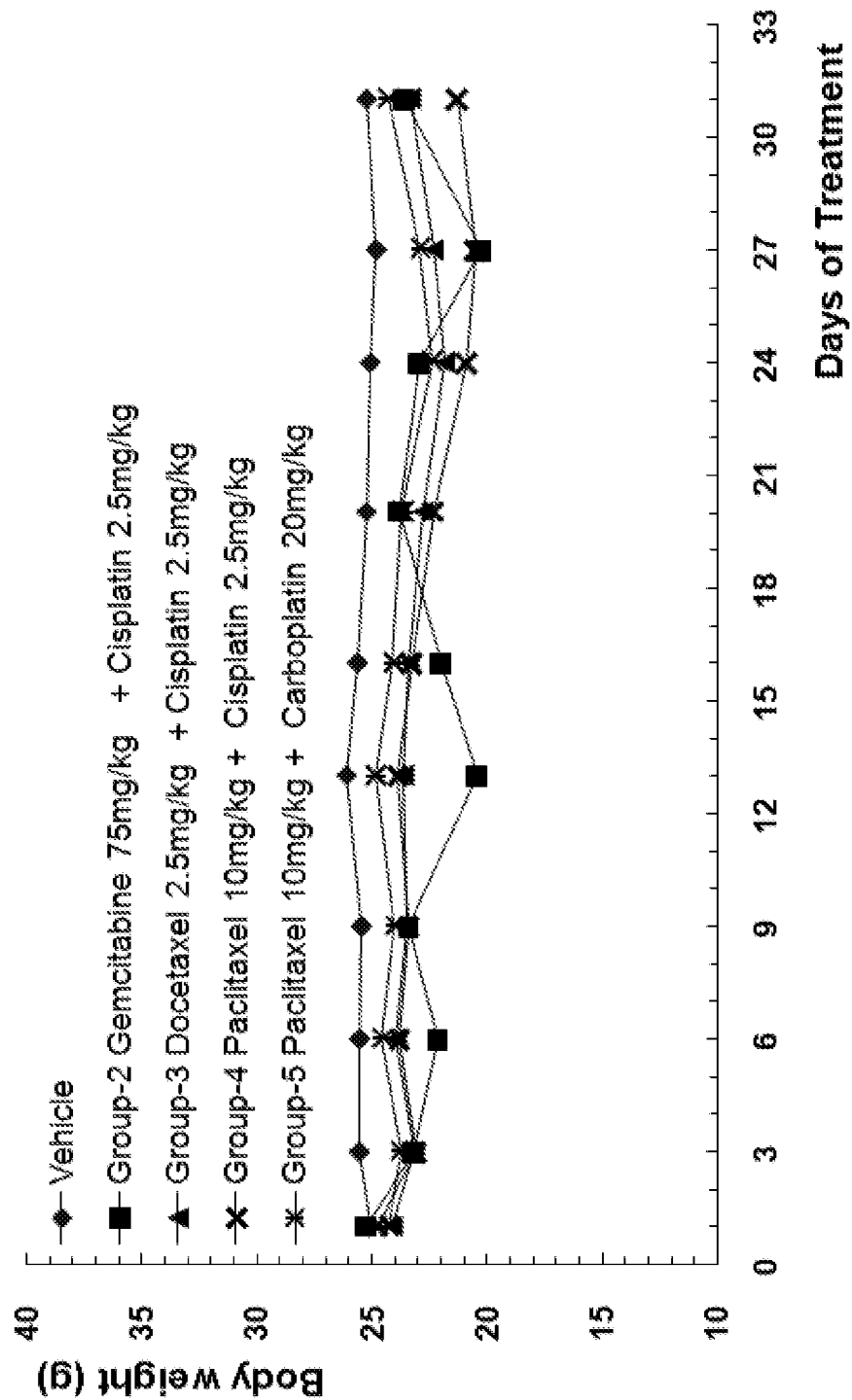
FIG. 18 is a graph showing the body weight of B-NDG mice after human primary lung carcinoma cells were injected into the B-NDG mice, and the mice were treated by (1) gemcitabine (75 mg/kg) and cisplatin (2.5 mg/kg), (2) docetaxel (2.5 mg/kg) and cisplatin (2.5 mg/kg), (3) paclitaxel (10 mg/kg) and cisplatin (2.5 mg/kg), or (4) paclitaxel (10 mg/kg) and carboplatin (20 mg/kg).
Figure 19:
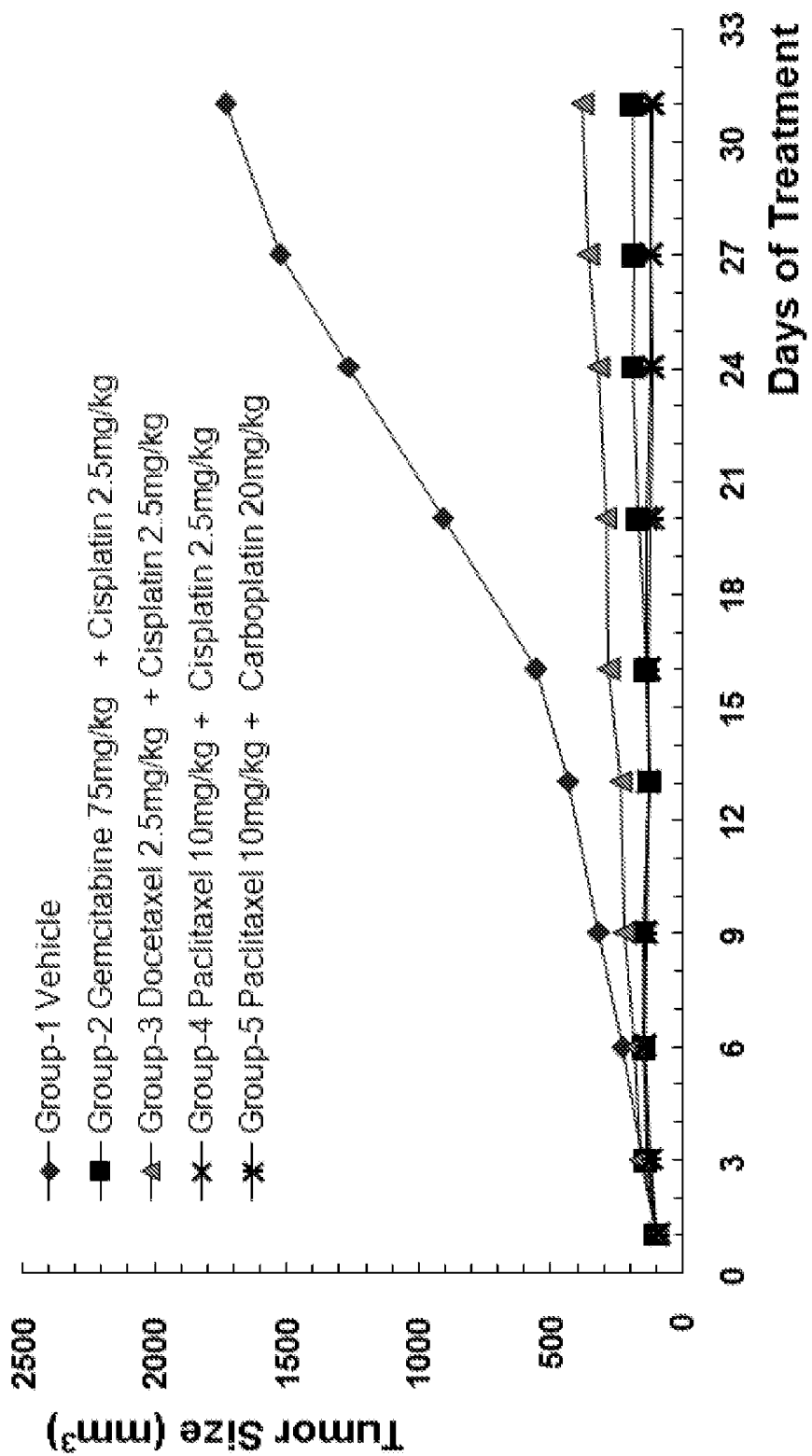
FIG. 19 is a graph showing the tumor size in B-NDG mice after human primary lung carcinoma cells were injected into the B-NDG mice, and the mice were treated by (1) gemcitabine (75 mg/kg) and cisplatin (2.5 mg/kg), (2) docetaxel (2.5 mg/kg) and cisplatin (2.5 mg/kg), (3) paclitaxel (10 mg/kg) and cisplatin (2.5 mg/kg), or (4) paclitaxel (10 mg/kg) and carboplatin (20 mg/kg).
Figure 20:
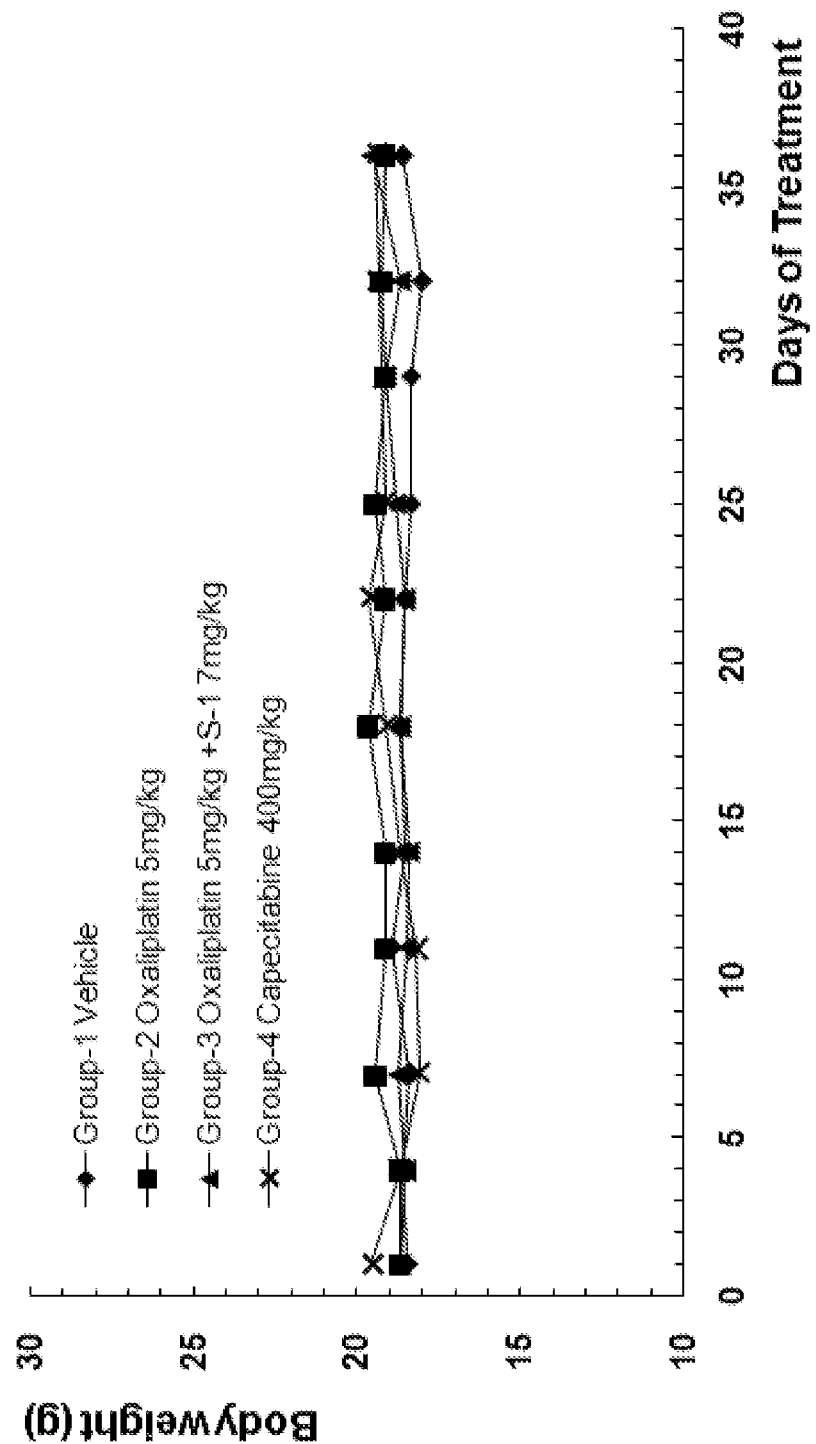
FIG. 20 is a graph showing the body weight of B-NDG mice after human primary gastric carcinoma cells were injected into the B-NDG mice, and the mice were treated by (1) oxaliplatin (5 mg/kg), (2) oxaliplatin (5 mg/kg) and S-1 (7 mg/kg), and (3) capecitabine (400 mg/kg).
Figure 21:
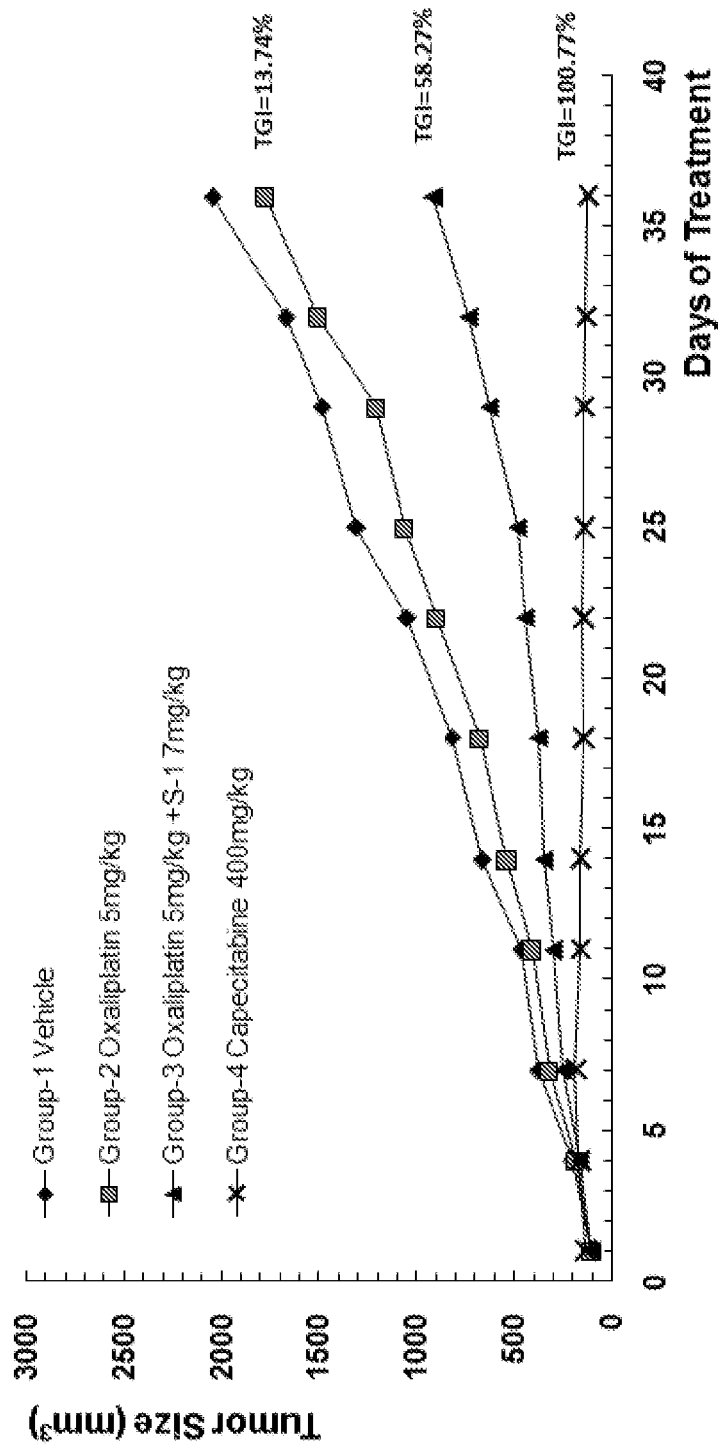
FIG. 21 is a graph showing the tumor size in B-NDG mice after human primary gastric carcinoma cells were injected into the B-NDG mice, and the mice were treated by (1) oxaliplatin (5 mg/kg), (2) oxaliplatin (5 mg/kg) and S-1 (7 mg/kg), and (3) capecitabine (400 mg/kg).
Figure 22:
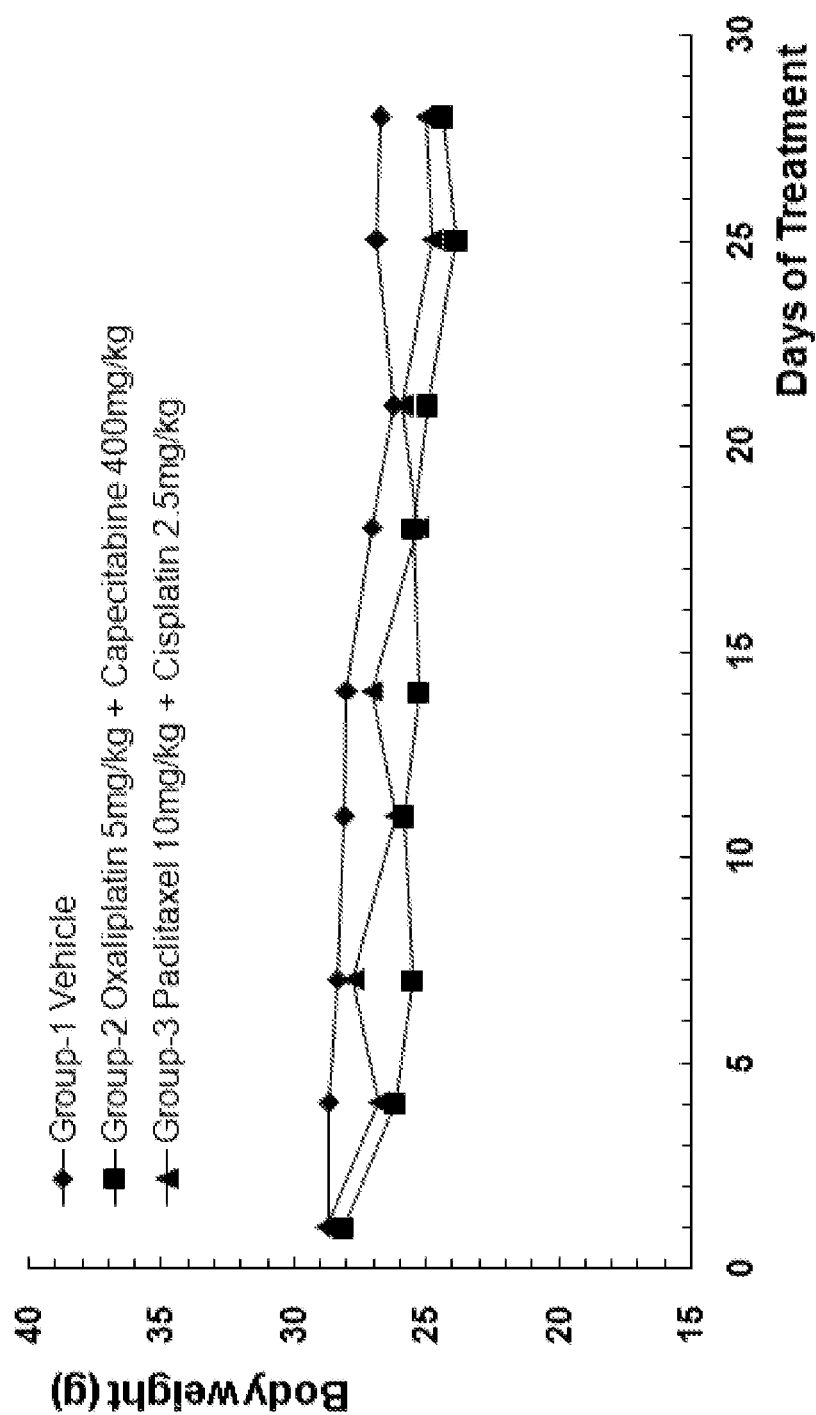
FIG. 22 is a graph showing the body weight of B-NDG mice after human primary gastric carcinoma cells were injected into the B-NDG mice, and the mice were treated by (1) oxaliplatin (5 mg/kg) and capecitabine (400 mg/kg), and (2) paclitaxel (10 mg/kg) and cisplatin (2.5 mg/kg).
Figure 23:
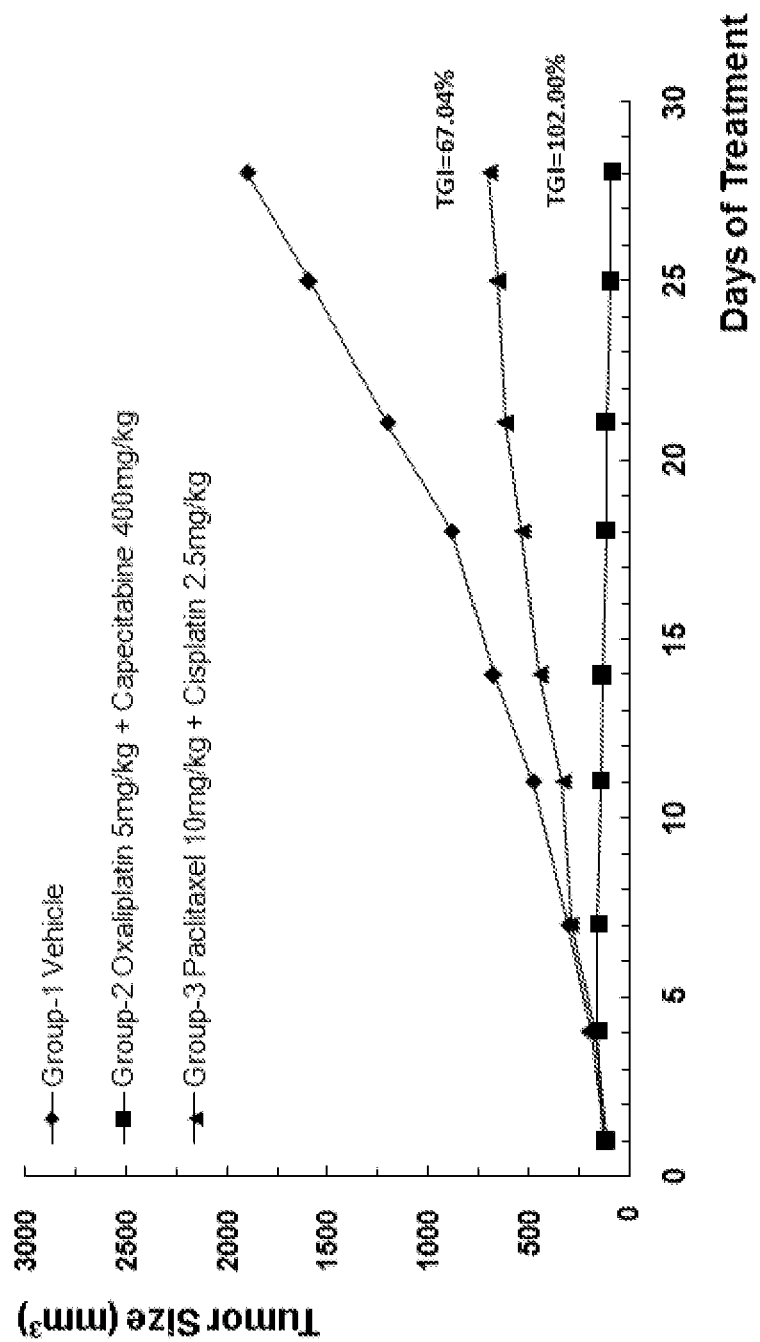
FIG. 23 is a graph showing the tumor size in B-NDG mice after human primary gastric carcinoma cells were injected into the B-NDG mice, and the mice were treated by (1) oxaliplatin (5 mg/kg) and capecitabine (400 mg/kg), and (2) paclitaxel (10 mg/kg) and cisplatin (2.5 mg/kg).

Overall, the animals in each group were generally healthy. Except in the control group, the body weights in the treatment groups increased over the course of the experiment. The body weights of the treatment group mice and the control group mice were not significantly different from each other, indicating that the antibodies were well tolerated and safe to use without obvious toxicity. Tumors in the control group mice continued to grow during the experimental period (FIG. 13). The fluorescent signals for tumor cells in the groups that were treated by AB1 (G2), AB2 (G3), and AB3 (G4) were obviously lower than the control group (G1), and were not the same. The results indicated that these antibodies had different tumor inhibitory effects, and AB1 had better tumor inhibitory effects than AB2 and AB3.

In NOD background mice, it is known that SIRPa can bind to human CD47, and human tumor cells can express CD47 and inhibit phagocytosis by macrophages. After anti-human CD47 antibody was administered to B-NDG mice, the anti-human CD47 antibody blocked the interaction between CD47 and SIRPa, increasing the phagocytic activities of macrophages, thereby killing the tumor cells. This experiment demonstrated that B-NDG mice can be used as in vivo models for drug screening and efficacy testing for human antibodies.

Example 13. Evaluating the Efficacy of Combination Therapies

Clinical studies have shown that chemotherapies have great efficacy on various human solid tumors, have broad spectrum of anti-tumor effects, and can work in synergy with multiple anti-tumor drugs without cross-resistance. At present, there are dozens of chemotherapeutic drugs. Since the mechanisms for the chemotherapeutic drug are different, the chemotherapeutic drug is often used with one or more additional anti-tumor agents. The B-NDG mice obtained by the methods as described herein can be used to screen drugs and test the efficacy of the combination therapies to identify the combination with the best efficacy.

For this purpose, several experiments were performed, and several different types of human tumor cells were injected to the mice. When the tumor formed in the mice, the mice were randomly divided to a control group and several treatment groups (n=5/group). The treatment groups were randomly selected for treatment with different combinations of chemotherapy agents.

The results (FIGS. 15, 17, 19, 21, and 23) showed that tumors of all control mice continued to grow during the experimental period, whereas tumors in the treatment mouse group reduced or disappeared, indicating that the combination therapies can inhibit tumor growth, and these combination therapies had different tumor inhibitory effects.

As shown in FIGS. 14, 16, 18, 20, and 22, the body weights of the control and treated mice had little difference, indicating that the B-NDG mice tolerated the drug or the combination of drugs well, but the body weight of mice in certain treatment groups was significantly reduced (e.g., Group 3 in Experiment 1). This indicates that some drugs or combination of drugs may have stronger toxicities. The experimental designs, drug combinations, and doses are shown in Table 9.

TABLE 9

Experimental designs

| Experiment | Tumor cells | Control groups and treatment groups |
|---|---|---|
| 1 | Human primary lung carcinoma | Group-1 (Control): Vehicle (blank solution)<br>Group-2: Paclitaxel 10 mg/kg + Cisplatin 2.5 mg/kg<br>Group-3: Paclitaxel 10 mg/kg + Carboplatin 20 mg/kg<br>Group-4: Pemetrexed 100 mg/kg + Cisplatin 2.5 mg/kg |
| 2 | Human primary lung carcinoma | Group-1(Control): Vehicle (blank solution)<br>Group-2: 5-FU 20 mg/kg<br>Group-3: Gemcitabine 75 mg/kg + 5-FU 20 mg/kg<br>Group-4: Gemcitabine 75 mg/kg + Oxaliplatin 5 mg/kg |
| 3 | Human primary lung carcinoma | Group-1 (Control): Vehicle (blank solution)<br>Group-2: Gemcitabine 75 mg/kg + Cisplatin 2.5 mg/kg<br>Group-3: Docetaxel 2.5 mg/kg + Cisplatin 2.5 mg/kg<br>Group-4: Paclitaxel 10 mg/kg + Cisplatin 2.5 mg/kg<br>Group-5: Paclitaxel 10 mg/kg + Carboplatin 20 mg/kg |
| 4 | Human primary gastric carcinoma | Group-1 (Control): Vehicle (blank solution)<br>Group-2: Oxaliplatin 5 mg/kg<br>Group-3: Oxaliplatin 5 mg/kg + S-1 7 mg/kg<br>Group-4: Capecitabine 400 mg/kg |
| 5 | Human primary gastric carcinoma | Group-1(Control): Vehicle (blank solution)<br>Group-2: Oxaliplatin 5 mg/kg + Capecitabine 400 mg/kg<br>Group-3: Paclitaxel 10 mg/kg + Cisplatin 2.5 mg/kg |

Example 14. Patient-Derived Xenograft (PDX) Models

Human patients' tumor tissues can be transplanted to the B-NDG immunodeficient mice obtained by the methods described herein to obtain Patient-derived Xenograft (PDX) tumor models. Because these tumor tissues are derived from humans, these models are more relevant to clinic use.

In this example, fresh lung cancer tissue samples were collected from four patients and were transplanted into B-NDG mice (4-6 weeks). When the tumor size reached 500-1000 mm$^3$, the transplanted tumors were passaged to the next generation of mice. The procedure was repeated. The second or third generation of mice, or later generations of mice were selected for experiments.

Figure 24:
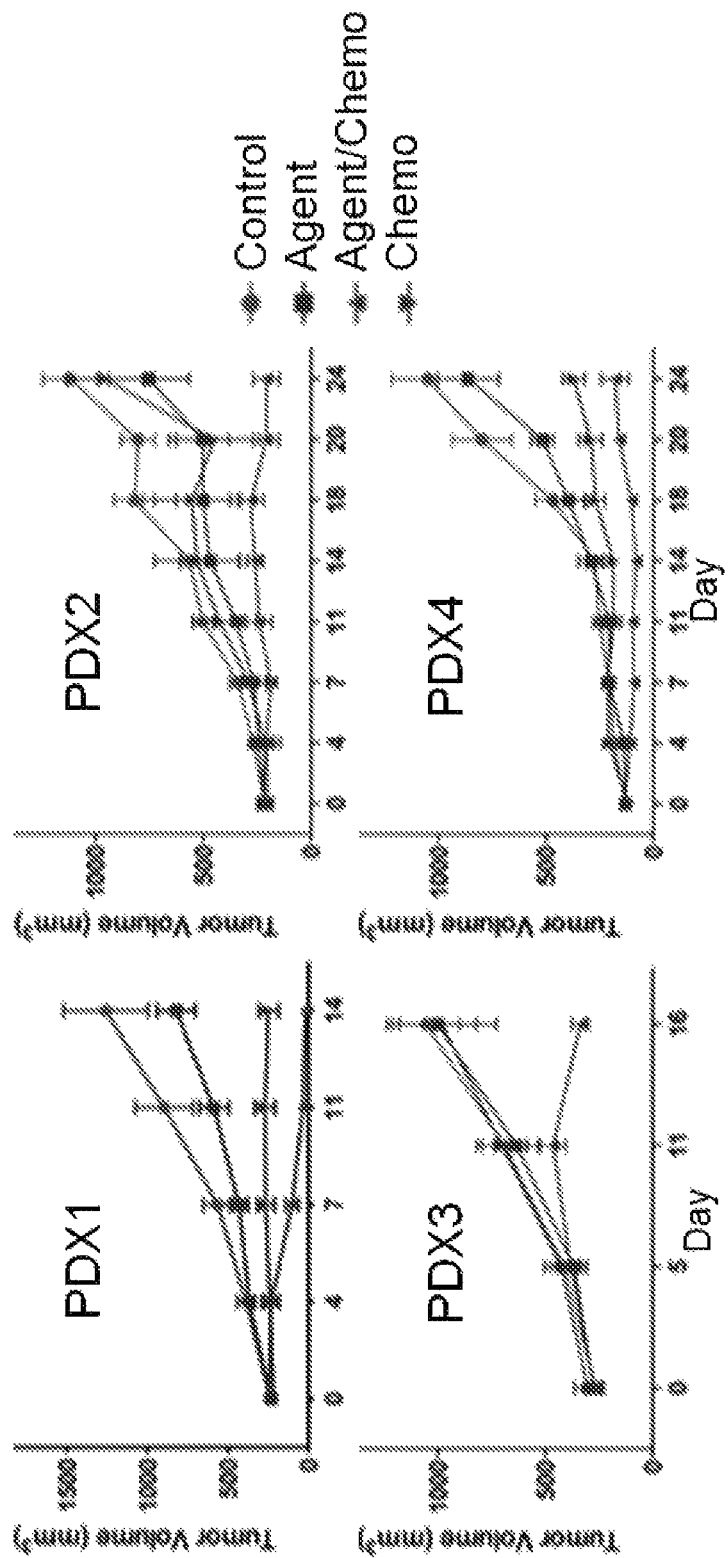
FIG. 24 is a set of graphs showing the tumor size in B-NDG mice. The lung cancer samples were collected from four different patients and were transplanted into four B-NDG mouse groups respectively. The mice in each group were further divided, and treated by an antibody, a chemotherapeutic agent, or the combination of the antibody and the chemotherapeutic agent.

The PDX mice were randomly divided into the control group and treatment groups (n=5/group). The treatment groups were treated by antibody A for treating human lung cancer, chemotherapeutic agent C, or the combination of antibody A and chemotherapeutic agent C. The control group was injected with a blank solution. Despite that all PDX mice were lung cancer PDX models, tumors in the PDX mice responded differently to these treatments (FIG. 24).

Example 15. Using B-NDG Immunodeficient Mice to Prepare Mouse Models with Additional Gene Modifications The B-NDG immunodeficient mouse obtained by the methods described herein can be further gene edited or mated with a mouse model with some other gene modifications.

In this example, B2m gene was directly knocked out by gene editing in the B-NDG immunodeficient mouse. PCR was performed to determine whether B2m gene was successfully knocked out. The sequences for the PCR primers are shown below:

```
Upstream primer (SEQ ID NO: 16):
5'-GAATAAATGAAGGCGGTCCCAGGCT-3';

Downstream primer (SEQ ID NO: 17):
5'-AAACCCATGCAGGCTGTGTAACTGA-3'.
```

Figure 25:
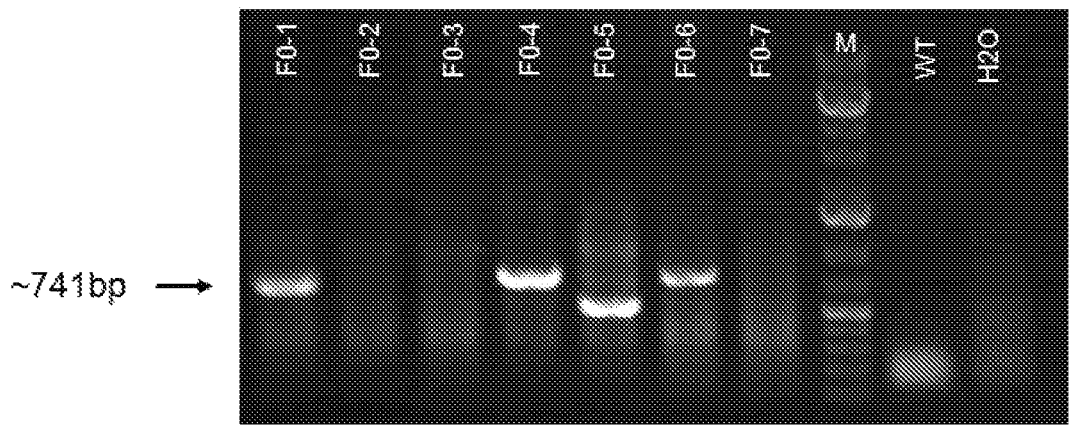
FIG. 25 shows the PCR results for B-NDG mice with B2m knockout.

The PCR results for mouse tail genomic DNA are shown in FIG. 25. The mice labeled with FO-1, FO-4, FO-5, and FO-6 were B-NDG mice with B2m gene knockout.

Figure 26:
FIG. 26 is a photo of B-NDG nude mouse.

In addition, NOD/scid nude mice (Foxn1 knockout) were obtained by gene editing methods known in the art, and the mice were mated with B-NDG mice (or through in vitro fertilization). The heterozygous mice with Foxn1 gene knockout and CD132 gene knockout (NOD/scid background) were obtained, and then were mated with each other. Homozygous mice with Foxn1 gene knockout and CD132 gene knockout were obtained. A photograph of the resulting B-NDG nude mouse (with Foxn1 gene knockout) was shown in FIG. 26.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse or a progeny thereof, whose genome comprises a disruption in the mouse's endogenous CD132 gene, wherein the disruption of the endogenous CD132 gene comprises deletion of more than 150 nucleotides in exon 1;
deletion of the entirety of intron 1, exon 2, intron 2, exon 3, intron 3, exon 4, intron 4, exon 5, intron 5, exon 6, intron 6, exon 7, intron 7; and
deletion of more than 250 nucleotides in exon 8, wherein the disruption is performed by CRISPR associated protein 9 (Cas9) with sgRNAs that target SEQ ID NO: 3 and SEQ ID NO: 6.

2. A method of producing a genetically-modified mouse, the method comprising introducing CRISPR associated protein 9 (Cas9) or a nucleic acid encoding Cas9, an sgRNA that targets SEQ ID NO: 3, and an sgRNA that targets SEQ ID NO: 6 into an embryo of a mouse, thereby causing a disruption in the embryo's endogenous CD132 gene;
culturing the embryo; and
transplanting the embryo to a recipient mouse to produce the genetically-modified mouse.

3. The method of claim 2, wherein the embryo has NOD/scid mutation.

4. The method of claim 3, wherein the method further comprises establishing a stable mouse line from progenies of the genetically-modified mouse.

5. A genetically-modified mouse obtained from progenies of the genetically-modified mouse produced by the method of claim 2.

6. The mouse of claim 1, wherein the mouse is homozygous with respect to the disruption.

7. The mouse of claim 1, wherein the mouse is heterozygous with respect to the disruption.

* * * * *

SEQUENCE LISTING

<160> NUMBER OF SEQ ID NOS: 19

<210> SEQ ID NO 1

```
<211> LENGTH: 23
<212> TYPE: DNA
<213> ORGANISM: Artificial
<220> FEATURE:
<223> OTHER INFORMATION: sgRNA target sequence

<400> SEQUENCE: 1
ccaccggaag ctacgacaaa agg                                              23

<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2
tctctacagc gtggtttcta agg                                              23

<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3
ggcttgtggg agagtggttc agg                                              23

<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4
ccacgctgta gagagagggg ggg                                              23

<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5
aggggaggtt agcgtcactt agg                                              23

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
gaaatcgaaa cttagcccca agg                                              23

<210> SEQ ID NO 7
<211> LENGTH: 23
<212> TYPE: DNA
<213> ORGANISM: Artificial
<220> FEATURE:
<223> OTHER INFORMATION: sgRNA target sequence

<400> SEQUENCE: 7
```

```
gcagcctgca tagcccttac tgg                                          23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
ccctactcac cttggcaatc tgg                                          23

<210> SEQ ID NO 9
<211> LENGTH: 24
<212> TYPE: DNA
<213> ORGANISM: Artificial
<220> FEATURE:
<223> OTHER INFORMATION: sgRNA sequence

<400> SEQUENCE: 9
caccggcttg tgggagagtg gttc                                         24

<210> SEQ ID NO 10
<211> LENGTH: 24
<212> TYPE: DNA
<213> ORGANISM: Artificial
<220> FEATURE:
<223> OTHER INFORMATION: sgRNA sequence

<400> SEQUENCE: 10
aaacgaacca ctctcccaca agcc                                         24

<210> SEQ ID NO 11
<211> LENGTH: 25
<212> TYPE: DNA
<213> ORGANISM: Artificial
<220> FEATURE:
<223> OTHER INFORMATION: sgRNA sequence

<400> SEQUENCE: 11
caccggaaat cgaaacttag cccca                                        25

<210> SEQ ID NO 12
<211> LENGTH: 25
<212> TYPE: DNA
<213> ORGANISM: Artificial
<220> FEATURE:
<223> OTHER INFORMATION: sgRNA sequence

<400> SEQUENCE: 12
aaactggggc taagtttcga tttcc                                        25

<210> SEQ ID NO 13
<211> LENGTH: 132
<212> TYPE: DNA
<213> ORGANISM: Artificial
<220> FEATURE:
<223> OTHER INFORMATION: Synthesized sequence

<400> SEQUENCE: 13
gaattctaat acgactcact ataggggtc ttcgagaaga cctgttttag agctagaaat    60
agcaagttaa aataaggcta gtccgttatc aacttgaaaa agtggcaccg agtcggtgct  120
tttaaaggat cc                                                     132
```

```
<210> SEQ ID NO 14
<211> LENGTH: 25
<212> TYPE: DNA
<213> ORGANISM: Artificial
<220> FEATURE:
<223> OTHER INFORMATION: PCR primer

<400> SEQUENCE: 14
aagatagcct agagggaaaa ggtgg                                    25

<210> SEQ ID NO 15
<211> LENGTH: 25
<212> TYPE: DNA
<213> ORGANISM: Artificial
<220> FEATURE:
<223> OTHER INFORMATION: PCR primer

<400> SEQUENCE: 15
aggtagaaaa agggagggag aatcc                                    25

<210> SEQ ID NO 16
<211> LENGTH: 25
<212> TYPE: DNA
<213> ORGANISM: Artificial
<220> FEATURE:
<223> OTHER INFORMATION: PCR primer

<400> SEQUENCE: 16
gaataaatga aggcggtccc aggct                                    25

<210> SEQ ID NO 17
<211> LENGTH: 25
<212> TYPE: DNA
<213> ORGANISM: Artificial
<220> FEATURE:
<223> OTHER INFORMATION: PCR primer

<400> SEQUENCE: 17
aaacccatgc aggctgtgta actga                                    25

<210> SEQ ID NO 18
<211> LENGTH: 1663
<212> TYPE: DNA
<213> ORGANISM: Mus musculus

<400> SEQUENCE: 18
aggaaatgta tgggtgggga gggcttgtgg gagagtggtt cagggttctg acacagacta     60
cacccagaga aagaagagca agcaccatgt tgaaactatt attgtcacct agatccttct    120
tagtccttca gctgctcctg ctgagggcag ggtggagctc caaggtcctc atgtccagtg    180
cgaatgaaga catcaaagct gatttgatcc tgacttctac agcccctgaa cacctcagtg    240
ctcctactct gccccttcca gaggttcagt gctttgtgtt caacatagag tacatgaatt    300
gcacttggaa tagcagttct gagcctcagg caaccaacct cacgctgcac tataggtaca    360
aggtatctga taataataca ttccaggagt gcagtcacta tttgttctcc aaagagatta    420
cttctggctg tcagatacaa aaagaagata ccagctcta ccagacattt gttgtccagc    480
tccaggaccc ccagaaaccc cagaggcgag ctgtacagaa gctaaaccta cagaatcttg    540
tgatcccacg ggctccagaa aatctaaacac tcagcaatct gagtgaatcc cagctagagc    600
tgagatggaa aagcagacat attaaagaac gctgtttaca atacttggtg cagtaccgga    660
gcaacagaga tcgaagctgg acggaactaa tagtgaatca tgaacctaga ttctcccctgc    720
```

```
ctagtgtgga tgagctgaaa cggtacacat ttcgggttcg gagccgctat aacccaatct    780
gtggaagttc tcaacagtgg agtaaatgga gccagcctgt ccactggggg agtcatactg    840
tagaggagaa tccttccttg tttgcactgg aagctgtgct tatccctgtt ggaccatgg     900
ggttgattat taccctgatc tttgtgtact gttggttgga acgaatgcct ccaattcccc    960
ccatcaagaa tctagaggat ctggttactg aataccaagg gaacttttcg gcctggagtg   1020
gtgtgtctaa agggctgact gagagtctgc agccagacta cagtgaacgg ttctgccacg   1080
tcagcgagat tcccccaaaa ggaggggccc taggagaggg gcctggaggt tctccttgca   1140
gcctgcatag cccttactgg cctcccccat gttattctct gaagccggaa gcctgaacat   1200
caatcctttg atggaacctc aaagtcctat agtcctaagt gacgctaacc tcccctactc   1260
accttggcaa tctggatcca atgctcactg ccttcccttg gggctaagtt tcgatttcct   1320
gtcccatgta actgcttttc tgttccatat gccctacttg agagtgtccc ttgccctctt   1380
tccctgcaca agccctccca tgcccagcct aacacctttc cactttcttt gaagagagtc   1440
ttaccctgta gcccagggtg gctgggagct cactatgtag gccaggttgg cctccaactc   1500
acaggctatc ctcccacctc tgcctcataa gagttggggt tactggcatg caccaccaca   1560
cccagcatgg tccttctctt ttataggatt ctccctccct ttttctacct atgattcaac   1620
tgtttccaaa tcaacaagaa ataaagtttt taaccaatga tca                     1663
```

<210> SEQ ID NO 19
<211> LENGTH: 369
<212> TYPE: PRT
<213> ORGANISM: Mus musculus

<400> SEQUENCE: 19

```
Met Leu Lys Leu Leu Leu Ser Pro Arg Ser Phe Leu Val Leu Gln Leu
 1               5                  10                  15

Leu Leu Leu Arg Ala Gly Trp Ser Ser Lys Val Leu Met Ser Ser Ala
            20                  25                  30

Asn Glu Asp Ile Lys Ala Asp Leu Ile Leu Thr Ser Thr Ala Pro Glu
        35                  40                  45

His Leu Ser Ala Pro Thr Leu Pro Leu Pro Glu Val Gln Cys Phe Val
    50                  55                  60

Phe Asn Ile Glu Tyr Met Asn Cys Thr Trp Asn Ser Ser Ser Glu Pro
65                  70                  75                  80

Gln Ala Thr Asn Leu Thr Leu His Tyr Arg Tyr Lys Val Ser Asp Asn
                85                  90                  95

Asn Thr Phe Gln Glu Cys Ser His Tyr Leu Phe Ser Lys Glu Ile Thr
           100                 105                 110

Ser Gly Cys Gln Ile Gln Lys Glu Asp Ile Gln Leu Tyr Gln Thr Phe
       115                 120                 125

Val Val Gln Leu Gln Asp Pro Gln Lys Pro Gln Arg Arg Ala Val Gln
   130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
                165                 170                 175

Arg His Ile Lys Glu Arg Cys Leu Gln Tyr Leu Val Gln Tyr Arg Ser
            180                 185                 190

Asn Arg Asp Arg Ser Trp Thr Glu Leu Ile Val Asn His Glu Pro Arg
        195                 200                 205
```

```
Phe Ser Leu Pro Ser Val Asp Glu Leu Lys Arg Tyr Thr Phe Arg Val
    210             215                 220

Arg Ser Arg Tyr Asn Pro Ile Cys Gly Ser Ser Gln Gln Trp Ser Lys
225             230                 235                 240

Trp Ser Gln Pro Val His Trp Gly Ser His Thr Val Glu Glu Asn Pro
                245                 250                 255

Ser Leu Phe Ala Leu Glu Ala Val Leu Ile Pro Val Gly Thr Met Gly
            260                 265                 270

Leu Ile Ile Thr Leu Ile Phe Val Tyr Cys Trp Leu Glu Arg Met Pro
        275             280                 285

Pro Ile Pro Pro Ile Lys Asn Leu Glu Asp Leu Val Thr Glu Tyr Gln
    290             295                 300

Gly Asn Phe Ser Ala Trp Ser Gly Val Ser Lys Gly Leu Thr Glu Ser
305             310                 315                 320

Leu Gln Pro Asp Tyr Ser Glu Arg Phe Cys His Val Ser Glu Ile Pro
                325             330                 335

Pro Lys Gly Gly Ala Leu Gly Glu Gly Pro Gly Gly Ser Pro Cys Ser
                340             345                 350

Leu His Ser Pro Tyr Trp Pro Pro Pro Cys Tyr Ser Leu Lys Pro Glu
        355             360                 365

Ala
```